US011259936B2

(12) United States Patent
Betz et al.

(10) Patent No.: US 11,259,936 B2
(45) Date of Patent: Mar. 1, 2022

(54) INTRAVERTEBRAL IMPLANT SYSTEM AND METHODS OF USE

(71) Applicant: NOFUSCO Corporation, Bradenton, FL (US)

(72) Inventors: Randal R. Betz, Bradenton, FL (US); Dale E. Whipple, Nashua, NH (US)

(73) Assignee: NOFUSCO CORPORATION, Bradenton, FL (US)

( * ) Notice: Subject to any disclaimer, the term of this patent is extended or adjusted under 35 U.S.C. 154(b) by 0 days.

(21) Appl. No.: 17/347,492

(22) Filed: Jun. 14, 2021

(65) Prior Publication Data

US 2021/0386556 A1 Dec. 16, 2021

Related U.S. Application Data

(60) Provisional application No. 63/039,242, filed on Jun. 15, 2020.

(51) Int. Cl.
*A61F 2/44* (2006.01)
*A61F 2/30* (2006.01)

(52) U.S. Cl.
CPC .. *A61F 2/4425* (2013.01); *A61F 2002/30405* (2013.01); *A61F 2002/443* (2013.01)

(58) Field of Classification Search
CPC .. A61F 2/4425; A61F 2002/443; A61B 17/70; A61B 17/7047
See application file for complete search history.

(56) References Cited

U.S. PATENT DOCUMENTS

| 5,947,969 | A | | 9/1999 | Errico et al. | |
|---|---|---|---|---|---|
| 5,980,522 | A | * | 11/1999 | Koros | A61F 2/446 623/17.11 |
| 6,527,803 | B1 | * | 3/2003 | Crozet | A61F 2/442 623/17.11 |

(Continued)

OTHER PUBLICATIONS

Ahn, J., Tabaraee, E., Bohl, D.D., Singh, K., Surgical management of adult spinal deformity: Indications, surgical outcomes, and health-related quality of life. Seminars in Spine Surgery, 29(2), 72-76, 2017, 5 pgs., https://doi.org/10.1053/j.semss.2016.12.001, Chicago, IL, USA.

(Continued)

*Primary Examiner* — Kevin T Truong
*Assistant Examiner* — Tracy L Kamikawa
(74) *Attorney, Agent, or Firm* — John Brooks Law LLC; John J. Brooks, III

(57) ABSTRACT

A vertebral implant device is described comprising a wedge, a plate having an external surface configuration and one or more plate tine, a staple having one or more staple tine and a coupling device. The coupling devices is configured to couple the wedge, the plate and the staple whereby when the vertebral implant is secured in a vertebral body, the external surface configuration of the plate alters the relative orientation of a superior endplate surface plane and an inferior endplate surface plane of the vertebral body and alters the alignment of the spine. In some embodiments, plate tines and staple tine are configured to frictionally engage the vertebral body. In some embodiments, the coupling device is a screw and a nut. In some embodiments, interchangeable wedges are used to provide multiple implant device configurations.

19 Claims, 19 Drawing Sheets

(56) References Cited

U.S. PATENT DOCUMENTS

| | | | |
|---|---|---|---|
| 6,623,484 B2* | 9/2003 | Betz | A61B 17/7044 |
| | | | 606/279 |
| 7,833,245 B2 | 11/2010 | Kaes | |
| 8,097,037 B2 | 1/2012 | Serhan | |
| 8,273,129 B2* | 9/2012 | Baynham | A61F 2/447 |
| | | | 623/17.16 |
| 9,055,981 B2* | 6/2015 | Lamborne | A61B 17/7065 |
| 10,588,753 B2 | 3/2020 | Whipple et al. | |
| 2005/0165485 A1 | 7/2005 | Trieu | |
| 2014/0100662 A1 | 4/2014 | Patterson et al. | |

OTHER PUBLICATIONS

Magerl, F., Aebi, M., Gertzbein, S.D., Harms, J. Nazarian, S., A comprehensive classification of thoracic and lumbar injuries. European Spine Journal, 3(4), 184-201, 1994, 18 pgs., https://doi.org/10.1007/BF02221591.

Yang, Andres, Non-FInal Office Action for co-pending U.S. Appl. No. 15/402,112, dated Aug. 29, 2018, 9 pgs., USPTO, Alexandria VA, USA.

James Guille, The Feasibility, Safety, and Utility of Vertebral Wedge Osteotomies for the Fusionless Treatment of Paralytic Scoliosis SPINE vol. 28 Number 20s pp. S266-S274, 9 pgs., 2003, Lippincott Williams & Wlkins, Inc, USA.

Kevin Mccarthy, Clinical Efficacy of the Vertebral Wedge Osteotomy for the Fusionless Treatment of Paralytic Scoliosis SPINE vol. 35 Number 4 pp. 403-410, 8 pgs., 2010 Lippincott, Williams & Wilkins, Inc., USA.

Betz RR; Cunningham B; Selgrath C; Drwery T; Sherman MC: Preclinical testing of a wedge-rod system for fusionless correction of scoliosis. Spine (Phila Pa 1976) 28(20S):S275-S278, 2003, 4 pgs., Philadelphia PA, USA.

Betz RR; Mulcahey MJ: New surgical treatments for scoliosis: vertebral body stapling and wedge osteotomies. Viewpoint, Shriners Hospitals for Children, www.shrinershq.org, Sep. 2001, as downloaded from www.SpineUniverse.com on Oct. 15, 2018,4 pgs., USA.

Didelot, William P.; Kling, Thomas F. Jr.; Lindseth, Richard E.: Anterior Vertebral Osteotomies to Correct Lumbar Scoliosis Without Fusion, Ch. 47. In: Modern Anterior Scoliosis Surgery (Lenke, L.; Betz, R.; Harms, J., eds.), Thieme Medical Publishers, 2004, pp. 693-706, 7 pgs. (2 pgs per sheet), New York, USA.

Rodriquez, Kari, Written Opinion of the International Searching Authority for co-pending PCT Application No. PCT/US21/37285, Aug. 24, 2021, 7 pgs.. United States Patent and Trademark Office, Alexandria, VA, USA.

Rodriquez, Kari, International Search Report for co-pending PCT Application No. PCT/US21/37285, Aug. 24, 2021, 2 pgs., United States Patent and Trademark Office, Alexandria, VA, USA.

\* cited by examiner

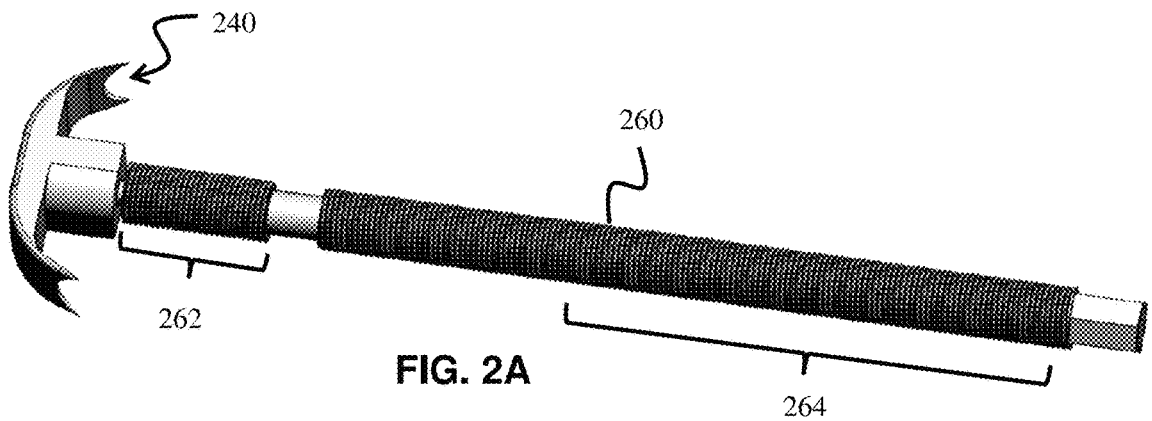
FIG. 2A
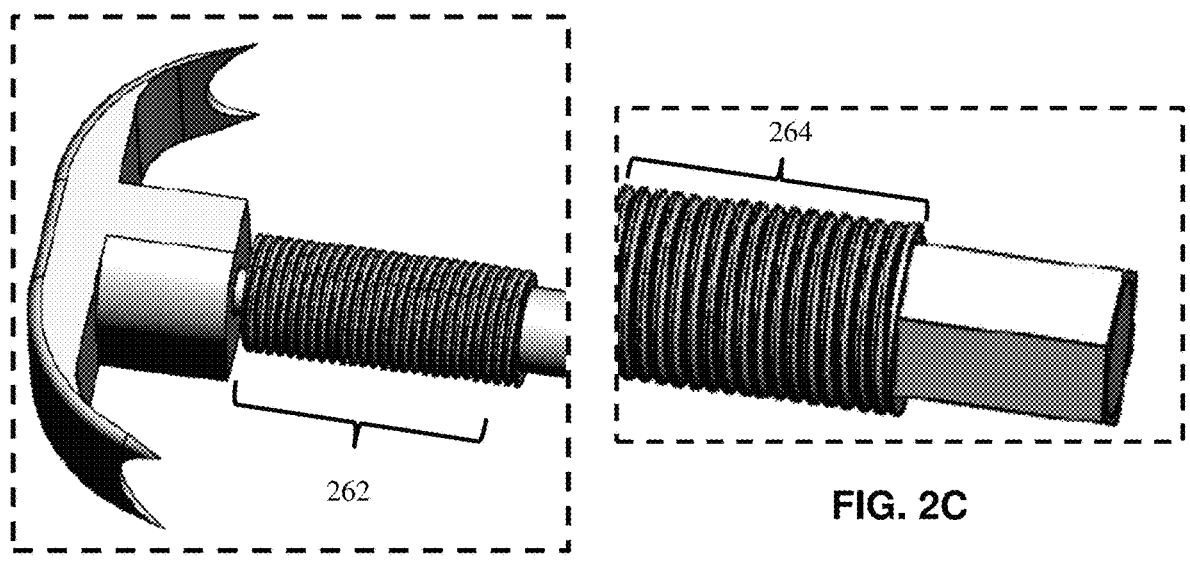
FIG. 2B
FIG. 2C
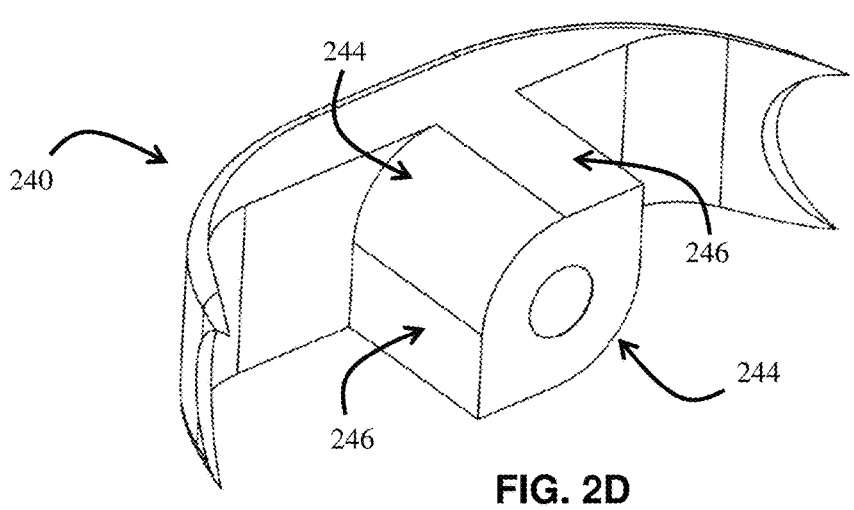
FIG. 2D

Table A
Coronal and Sagittal Correction

| Insertion Approach | Spinal Area | Plate Dimension Width Ranges (Transverse in mm) | Plate Dimension Length Ranges Proximal End to Distal End (mm) | Plate Dimension Height Ranges of Surface Top Surface to Bottom Surface at Proximal End with Wedge Inserted (mm) | Plate Transverse Angle Range (Along Width of Surface Plane, in Degrees) | Wedge Longitudinal Angle Range (Along Length of Surface Planes in Degrees) | Alignment Effect: Vertebrae Surface Alteration in Coronal Plane (Degrees) | Alignment Effect: Vertebrae Surface Alteration in Sagittal Plane (Degrees) | Alignment Effect: Wedged Vertebrae Correction (WVC) Foraminal Stenosis Correction (FSC) |
|---|---|---|---|---|---|---|---|---|---|
| Lateral | Lumbar | 15, 20 | 40, 45, 50, 55 | 5, 10, 15 | 0, 5, 10, 15, 20 | 5, 10, 15, 20 | 5, 10, 15, 20 | 0, 5, 10, 15, 20 | WVC and FSC |
| Lateral | Thoracic | 10 | 25, 30, 35 | 2.5, 5, 7.5, 10 | 0, 5, 10 | 5, 10, 15 | 5, 10, 15 | 0, 5, 10 | WVC |
| Oblique | Lumbar | 15, 20 | 40, 45, 50, 55 | 5, 10, 15 | 0, 5, 10, 15, 20 | 5, 10, 15, 20 | 5, 10, 15, 20, 25, 30 | 5, 10, 15, 20, 25, 30 | WVC and FSC |
| Oblique | Thoracic | 10 | 25, 30, 35 | 2.5, 5, 7.5, 10 | 0, 5, 10 | 5, 10, 15 | 5, 10, 15, 20, 25 | 5, 10, 15, 20, 25 | WVC |
| Oblique | Cervical | 8 | 17.5, 20, 25 | 2.5, 5 | 0, 2.5, 5 | 2.5, 5, 7.5 | 2.5, 5, 7.5, 10, 12.5 | 2.5, 5, 7.5, 10, 12.5 | FSC |
| Anterior | Lumbar | 15, 20 | 40, 45, 50, 55 | 5, 10, 15 | 0, 5, 10, 15, 20 | 5, 10, 15, 20 | 0, 5, 10, 15, 20 | 5, 10, 15, 20 | WVC and FSC |
| Anterior | Thoracic | 10 | 25, 30, 35 | 2.5, 5, 7.5, 10 | 0, 5, 10 | 5, 10, 15 | 0, 5, 10 | 5, 10, 15 | WVC |
| Anterior | Cervical | 8 | 17.5, 20, 25 | 2.5, 5 | 0, 2.5, 5 | 2.5, 5, 7.5 | 0, 2.5, 5 | 2.5, 5, 7.5 | FSC |

FIG. 6

INTRAVERTEBRAL IMPLANT SYSTEM AND METHODS OF USE

CROSS-REFERENCE TO RELATED APPLICATIONS

This application claims benefit to U.S. Patent App. No. 63/039,242, filed on Jun. 15, 2020, entitled "INTRAVERTEBRAL IMPLANT AND METHODS OF USE".

STATEMENT REGARDING FEDERALLY SPONSORED RESEARCH OR DEVELOPMENT

Not Applicable.

REFERENCE TO SEQUENCE LISTING, A TABLE, OR A COMPUTER PROGRAM LISTING COMPACT DISC APPENDIX

Not Applicable.

BACKGROUND

1. Field of the Invention

This invention relates to spinal implants, in particular an intravertebral implant configured to alter the alignment of a mammalian spine.

2. Background

In the field of spinal correction, available literature supports that trauma and degenerative spinal conditions resulting in back pain and leg pain lead to debilitation, loss of work and life happiness.

Compression fractures account for more than 60% of thoracolumbar fractures. Types of injuries associated with this type of injury may include: endplate impaction, wedge impaction fractures, vertebral body collapse, split fractures and coronal split fractures.

Patients with spine issues all start with collapsing of the disc, which happens due to loss of nutrition as aging occurs, which leads to loss of normal cushioning. Next, the endplates can no longer handle normal stress on the endplates, which leads to microfractures in the adjacent vertebral bodies. The chronic factures in a collapsed or fractured vertebral body may then create a cascade of other conditions in the spine, including (but not limited to) degenerative scoliosis, facet joint subluxation and facet joint degeneration, nerve root compression, and further vertebral body collapse.

Studies have also shown that degenerative disc disease and degenerative scoliosis may be associated with significant pain, mental anguish, anxiety, and functional disability as well as diminished self-perception/mental health and decreased function.

Patients with degenerative disc disease associated with degenerative scoliosis many times have a collapsing foramen on the concave slide of the spine. As this happens the superior facet of the vertebra below slides cephalad and pinches the nerve root in the now narrowed foramen. There is no good minimal surgical treatment with lasting symptom relief available in 2021. Common treatments are decompression without fusion, decompression with limited fusion, and extended (extensive) fusion and reconstruction.

Decompression without Fusion Treatments: A collapsing disc and Vertebral body collapse, which allows the facet from below to come up into the foramen. and cause compression of the nerve root. Some surgeons take a minimalist approach and try to open the foramen by surgically removing parts of the facet joint and some disc to give the nerve root space. While the conservative decompressive procedure without a fusion may be appropriate for selected patients, studies have demonstrated "greater risk of deformity progression, poor outcomes, and higher rates of reoperations" in these cases. It is believed that this is due to failure to address the cause of the narrowed foramen that being subluxation of the facet joints secondary to further disc collapse and further microfractures in the vertebral body leading to further wedging, and the foramen gets narrower again.

Decompression with Limited Fusion Treatments: Decompression with limited fusion is applicable for patients whose symptoms are limited to specific and short segments (1-3 levels), but care must be taken in assessing and correcting the sagittal and coronal alignment.2 Patients with uncorrected misalignment many times have poor outcomes after decompression with limited fusion. Fusions of any kind in the lumbar spine can many times start a cascade of events by putting increase stress through transferring lumbar spine motion to the unfused segments of the spine resulting in more deterioration of the adjacent levels requiring further treatment which is usually additional fusion. This is referred to in the literature as adjacent level disease.

Extended Reconstruction Treatments: Extended reconstruction (>3 levels) of the lumbar spine has been a foundation of correction for adult degenerative scoliosis. Fusions of this scope starts a cascade of events by putting increase stress through transferring lumbar spine motion to the unfused segments of the spine resulting in more deterioration of the adjacent levels requiring further treatment which is usually additional fusion. Clinical presentation of adjacent segment deterioration, with coronal, sagittal or both deformities above or below causing severe back pain often occur necessitating further additional levels requiring fusion.

Accordingly, there is need for an intravertebral implant system and methods of use to treat chronic trauma and fractures resulting in collapsed vertebra and causing back pain and or leg pain that addresses the above shortcomings.

BRIEF SUMMARY OF THE INVENTION

The following summary is included only to introduce some concepts discussed in the Detailed Description below. This summary is not comprehensive and is not intended to delineate the scope of protectable subject matter, which is set forth by the claims presented at the end.

The disclosed intravertebral implant system is intended to treat collapse of the vertebral body wedging, which is the result of microfractures of the vertebral body endplates. These microfractures occur because of the collapsed disc creates abnormal stress areas in the vertebral body. The vertebral body wedging, secondary to the microfractures, creates a coronal deformity and causing back pain thru misaligned facet joints. The source of the back pain can be confirmed by diagnostic local anesthetic agents around the painful facet joint. Correction of the coronal deformity in the vertebral body will reduce the back pain by realigning the facet joints in this select group of patients. This is analogous to the use of high tibial osteotomies for treatment of knee arthritis. The implant design allows for careful and patient-specific sagittal and coronal alignment to prevent the clinical outcomes of misalignment This osteotomy procedure and intravertebral implant device can relieve pain symptoms while maintaining lumbar spine mobility and prevent or delay adjacent level disease. The implant device does not have any motion itself. The implant device stabilizes a corrected vertebral body for 12 weeks while it heals.

With the disclosed intravertebral implant system, a vertebral body osteotomy with the intravertebral implant device can correct the wedged segment of the spine through the vertebral body. This opens the foramen and relieves the pinched nerve and therefore relieves the patient's radiculopathy symptoms. The implant design allows for careful and patient-specific sagittal and coronal alignment to prevent the clinical outcomes of misalignment.

This technology will lead to an improved quality of life when compared to current standard surgical techniques and technology when used as part of a decompression strategy. The patient will have relief from back and/or leg pain without a loss of spine mobility, which can significantly reduce or eliminate the risk of adjacent level accelerated degeneration in the other levels of the spine. The custom alignment that can be created with the implant device can prevent the clinical outcomes of misalignment.

In one embodiment, an intravertebral implant configured to alter an alignment of a spine is provided comprising a wedge, a plate having an external surface configuration and one or more plate tine, a coupling device, a staple having one or more staple tine, the one or more plate tine and the one or more staple tine are configured to frictionally engage a vertebral body, and the coupling device is configured to couple the wedge, the plate and the staple whereby when the vertebral implant is secured in the vertebral body, the external surface configuration of the plate alters a relative orientation of a superior endplate surface plane and an inferior endplate surface plane of the vertebral body and alters the alignment of the spine. In some embodiments, the coupling device is configured to adjust a device length of the vertebral implant device whereby an adjustment of the device length secures the one or more staple tine to a side wall of the vertebral body and secures the one or more plate tine to an opposing side wall of the vertebral body. In some embodiments, the coupling device comprises a screw and a nut, the screw further comprises a screw swivel coupler, and the staple comprises a staple swivel coupler to mate with the screw swivel coupler whereby the staple is configured to swivel about a longitudinal axis of the screw. In some embodiments, the external surface configuration of the plate is defined by a plate longitudinal angle between a longitudinal surface plane of a superior surface of the plate and a longitudinal surface plane of an inferior surface of the plate, and a plate height proximal to the one or more plate tine. In some embodiments, the external surface configuration of the plate is further defined by a plate transverse angle between a transverse surface plane of a superior surface of the plate and a transverse surface plane of an inferior surface of the plate. In some embodiments, an external surface configuration of the wedge is defined by a wedge longitudinal angle between a longitudinal surface plane of a superior surface of the wedge and a longitudinal surface plane of an inferior surface of the wedge, and a wedge height proximal to the one or more wedge tine. In some embodiments, the external surface configuration of the wedge is further defined by a wedge transverse angle between a transverse surface plane of a superior surface of the wedge and a transverse surface plane of an inferior surface of the wedge. In some embodiments the screw further comprises a drive portion configured to be engaged by a drive tool, the screw further comprises a distal threaded portion, the plate further comprises a threaded through hole to engage the distal threaded portion of the screw whereby when the drive portion is rotated in a first rotation direction by the drive, the screw adjusts the device length to a shorter length, and the staple further comprises a proximal end having a radiused corner profile whereby when the drive portion is rotated in the first rotation direction by the drive, the proximal end of the staple engages the vertebral body to position the one or more staple tine to engage the side wall of the vertebral body. In some embodiments, the coupling device is configured to adjust a device height of the vertebral implant device whereby an adjustment of the device height alters the external surface configuration of the plate and alters the relative orientation of a superior endplate surface plane and an inferior endplate surface plane of the vertebral body. In some embodiments, the coupling device comprises a screw and a nut, the plate further comprises a two-pronged u-shaped body defining a cavity configured to receive the wedge and the screw, the screw is configured to be received in a bore of the wedge, and the nut is configured to be received in the bore of the wedge and couple to the screw whereby the screw and the nut secure the wedge in the cavity of the plate. In some embodiments, the two-pronged u-shaped body comprises an angularly flexible body, and the device height is affected by an external surface configuration of the wedge.

In some embodiments, the screw further comprises a screw swivel coupler and a drive portion, the staple comprises a staple swivel coupler to mate with the screw swivel coupler whereby the staple is configured to swivel about a longitudinal axis of the screw, and the staple further comprises a proximal end having a radiused corner profile whereby when the drive portion is rotated in a first rotation, the proximal end of the staple engages the vertebral body to stop a further rotation of the staple.

In some embodiments, the wedge comprises a plurality of wedges configured to be exchangeable with the plate, and each of the plurality of wedges having a different external surface configuration.

In some embodiments, a vertebral implant system configured to alter an alignment of a spine is provided comprising a nut, a screw, a staple having one or more tine, a plate having a cavity configured to receive a wedge and the screw, the wedge selected from a set of wedges, the set of wedges comprising at least a first wedge and a second wedge wherein the first wedge has a first external dimension and the second wedge has a second external dimension, and the plate configured to receive either the first wedge or the second wedge whereby: when the first wedge is received in the plate, a first implant device external dimension is created to alter a relative orientation of a superior endplate surface plane and an inferior endplate surface plane of a vertebral body and alter the alignment of the spine to a first degree, and when the second wedge is received in the plate, a second implant device external dimension is created to alter the relative orientation of a superior endplate surface plane and an inferior endplate surface plane of the vertebral body and alter the alignment of the spine to a second degree. In some embodiments, the plate comprises at least a first plate and a second plate wherein, the first plate has a first external dimension, the second plate has second external dimension, and the first plate and the second plate are exchangeable whereby: when the first wedge is received in the first plate, a third implant device external dimension is created to alter the relative orientation of a superior endplate surface plane and an inferior endplate surface plane of the vertebral body and alter the alignment of the spine to a third degree, and when the first wedge is received in the second plate, a forth implant device external dimension is created to alter the relative orientation of a superior endplate surface plane and an inferior endplate surface plane of the vertebral body and alter the alignment of the spine to a forth degree. In some embodiments, the plate comprises at least a first plate and a second plate, the first implant device external dimension is defined by: a first plate longitudinal angle between a longitudinal surface plane of a superior surface of the plate and a longitudinal surface plane of an inferior surface of the plate, and a first plate height; and the second implant device external dimension is defined by: a second plate longitudinal angle between a longitudinal surface plane of a superior surface of the plate and a longitudinal surface plane of an inferior surface of the plate, and a second plate height. In some embodiments, the first implant device external dimension is defined by: a first wedge longitudinal angle between a longitudinal surface plane of a superior surface of the first wedge and a longitudinal surface plane of an inferior surface of the first wedge, a plate thickness, and a plate height; and the second implant device external dimension is defined by: a second wedge longitudinal angle between a longitudinal surface plane of a superior surface of the second wedge and a longitudinal surface plane of an inferior surface of the second wedge, the plate thickness, and the plate height.

A method to alter an alignment of a spine is provided comprising performing an osteotomy procedure through a vertebral body inferior to a pedicle of the vertebral body, inserting a plate and a staple into a vertebral opening created by the osteotomy procedure, deploying the staple whereby the staple extends outside of the vertebral opening, rotating the staple whereby one or more staple tines are positioned general perpendicular to the osteotomy to engage a side wall of the vertebral body, tightening a screw coupled to the staple whereby the staple tines are drawn towards the plate and engage the side wall of the vertebral body, positioning a wedge over a proximal end of the screw and into a cavity of the plate, coupling a nut on the proximal end of the screw and into a bore of the wedge, tightening the nut on the screw whereby the plate is distracted by the wedge as it is drawn into the vertebral body, and further tightening the nut onto the screw whereby the wedge is secured within the cavity of the plate defining an external surface configuration of the plate to alter a relative orientation of a superior endplate surface plane and an inferior endplate surface plane of the vertebral body and alter the alignment of the spine. In some embodiments, the implant device is inserted from a lateral approach. In some embodiments, the implant device is inserted from an anterior approach. In some embodiments, the implant device is inserted from an oblique approach.

Other objects, features, and advantages of the techniques disclosed in this specification will become more apparent from the following detailed description of embodiments in conjunction with the accompanying drawings.

BRIEF DESCRIPTION OF THE SEVERAL VIEWS OF THE DRAWINGS

In order that the manner in which the above-recited and other advantages and features of the invention are obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIGS. 2A-2I show another example embodiment of a an intravertebral implant device showing additional details for the screw;

FIG. 5A shows a top view of an an example embodiment of an intravertebral implant device inserted from a lateral approach, FIG. 5B shows a top perspective view of an intravertebral implant device inserted from a lateral approach, and FIG. 5C shows a top view of an example embodiment an intravertebral implant device inserted from an oblique approach;

FIG. 6 includes Table A showing example characteristics of the intravertebral implant device components for use in correcting the coronal alignment of the spine;

DETAILED DESCRIPTION OF THE INVENTION

Figure 1A:
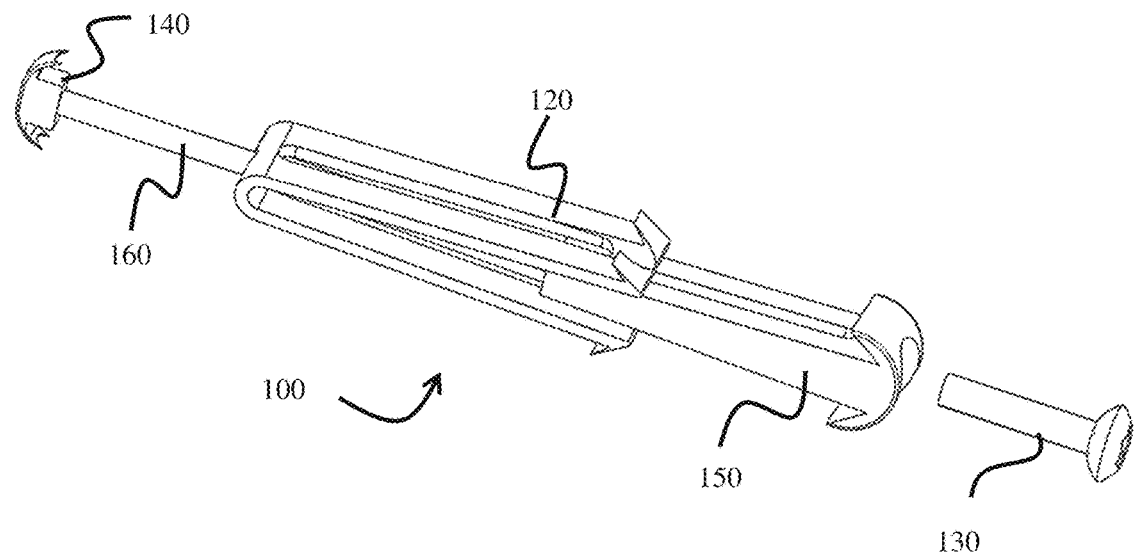
FIGS. 1A through 1K show example embodiments of an intravertebral implant device and example components.

COPYRIGHT NOTICE: A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever. The following notice applies to any software and data as described below and in the drawings hereto: Copyright © 2020-2021, NOFUSCO Corporation, All Rights Reserved.

Intravertebral implant systems and methods of use will now be described in detail with reference to the accompanying drawings. Notwithstanding the specific example embodiments set forth below, all such variations and modifications that would be envisioned by one of ordinary skill in the art are intended to fall within the scope of this disclosure.

Some embodiments of the intravertebral implant system is intended for use in the thoracolumbar spine (T11-L5) to replace a portion of and/or restore height of a collapsed, damaged, or unstable vertebral body due to trauma (i.e., fracture) or osteotomy. The system is to be placed unilaterally and used with autograft or allograft and may be used with supplemental spinal fixation as part of the device.

Some embodiments of the intravertebral implant system are intended to treat collapse of the vertebral body wedging, which is the result of microfractures of the vertebral body endplates. These microfractures occur because of the collapsed disc. The vertebral body wedging, secondary to the microfractures, creates a coronal deformity and causing back pain thru malaligned facet joints. The source of the back pain can be confirmed by diagnostic local anesthetic agents around the painful facet joint. Correction of the coronal deformity will reduce the back pain by realigning the facet joints in this select group of patients. This is analogous to the use of high tibial osteotomies for treatment of knee arthritis. The intravertebral implant system may be used as an adjunct to correct the spine coronal deformity in patients diagnosed with degenerative scoliosis.

This coronal deformity of the vertebrae may or may not be associated with leg radiculopathy from a narrowed foramen in addition to back pain as above or as a separate clinical problem. When the vertebra is wedged and the disc space collapses the facet joints sublux with the superior facet of the lower vertebra riding high in the foramen (narrowed foramen) pinching the exiting nerve root. This radiculopathy pain would be relieved by indirect decompression thru the osteotomy, placement of the intravertebral implant device indirectly opens the foramen through reducing the subluxed facet joints and then stabilizes the correction until healing of the vertebral body occurs in 12 weeks.

The disclosed intravertebral implant systems and methods will lead to an improved quality of life when compared to current standard surgical techniques and technology when used as part of a decompression strategy. The patient will have relief from back and/or leg pain without a loss of spine mobility, which will significantly reduce or eliminate the risk of adjacent level accelerated degeneration in the other levels of the spine. The custom alignment that can be created with the implant device can prevent the problematic clinical outcomes of misalignment.

When used as an intravertebral body fusion device the intravertebral implant system is intended for use in skeletally mature patients who have had six months of non-operative treatment. The implant device is intended for use at one level or two levels for the treatment of degenerative disc disease (DDD) with up to Grade I spondylolisthesis. This procedure and the intravertebral implant device treat some cases of back pain caused by malalignment of the facet joints secondary to collapse of degeneration of the disc confirmed by history, radiographic studies, and diagnostic facet joint injections with local anesthetic to confirm source of pain being from the malaligned facet joints. This is analogous to the use of high tibial osteotomies for treatment of knee arthritis. Additionally, the intravertebral implant system can be used as an adjunct to correct the spine coronal deformity in patients diagnosed with degenerative scoliosis. The intravertebral implant system is intended for use with or without supplemental fixation.

The intravertebral implant system is intended to treat collapse of the disc and vertebral body creating a coronal deformity and causing back pain thru malaligned facet joints. The source of the back pain can be confirmed by diagnostic local anesthetic agents around the painful facet joint. This coronal deformity may or may not be associated with leg radiculopathy from a narrowed foramen. This radiculopathy pain could be relieved by indirect decompression thru the osteotomy and placement of intravertebral implant system which opens the foramen and then stabilizes the correction until healing of the vertebral body occurs in 12 weeks.

One Example Embodiment of the Intravertebral Implant System:

In some embodiments, the intravertebral implant system comprises an intravertebral implant device. For illustration purposes and not for limitation, one example embodiment of the intravertebral implant device is shown in FIGS. 1A-1K.

As shown in FIG. 1A, the intravertebral implant system generally comprises an intravertebral implant device comprising, from a distal end to a proximal end, a staple 140, a plate 120, a wedge 150 and a coupling device. In the embodiment shown, the coupling device is a screw 160 that mates with a nut 130.

Figure 1B:
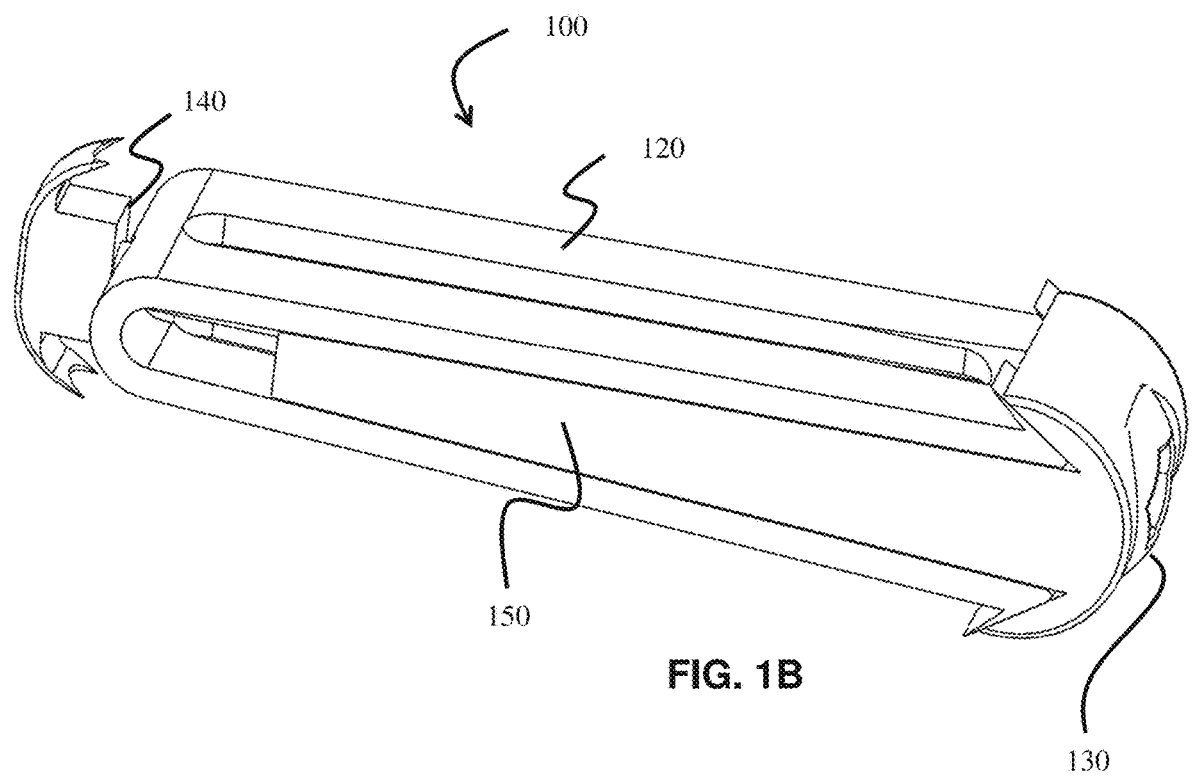

FIG. 1B shows a perspective view of an example embodiment of the intravertebral implant device assembled as in an inserted position. The intravertebral implant device is configured to be inserted completely within a vertebral body. As shown, the staple 140 is rotatably coupled to the distal end of the screw (see FIG. 1A 160). The distal end of the screw is positioned through an opening (not shown) on the distal end of the plate 120. The screw is also positioned through a bore (not shown) in the wedge 150. The nut 130 is also positioned through the bore of the wedge 150 so that its distal end can be coupled with the proximal end of the screw 160.

In one example embodiment, all of the components of the intravertebral implant device are made of a surgical grade metal such as Titanium (e.g., ASTM F136 Wrought 6Al4V Ti for Implant). The intravertebral implant device may be manufactured utilizing conventional machining technology i.e. milling and turning, mass media and/or electropolish finishing, color anodizing and passivation.

When assembled and implanted in the vertebral body, the external surface dimensions and configuration of the intravertebral implant device is able to correct the relative orientation of a superior endplate surface plane and an inferior endplate surface plane of a vertebral body to alter the alignment of the spine. The external surface configuration of the intravertebral implant device may be altered by using different configuration of intravertebral implant device components. For example, the wedge may be configured to have different surface angles to create different external surface configuration when mated with the plate. And sets of multiple exchangeable wedge configurations can provide implant device options to accommodate different vertebrae, different sized patients and different orientations of insertion.

Figure 1C:
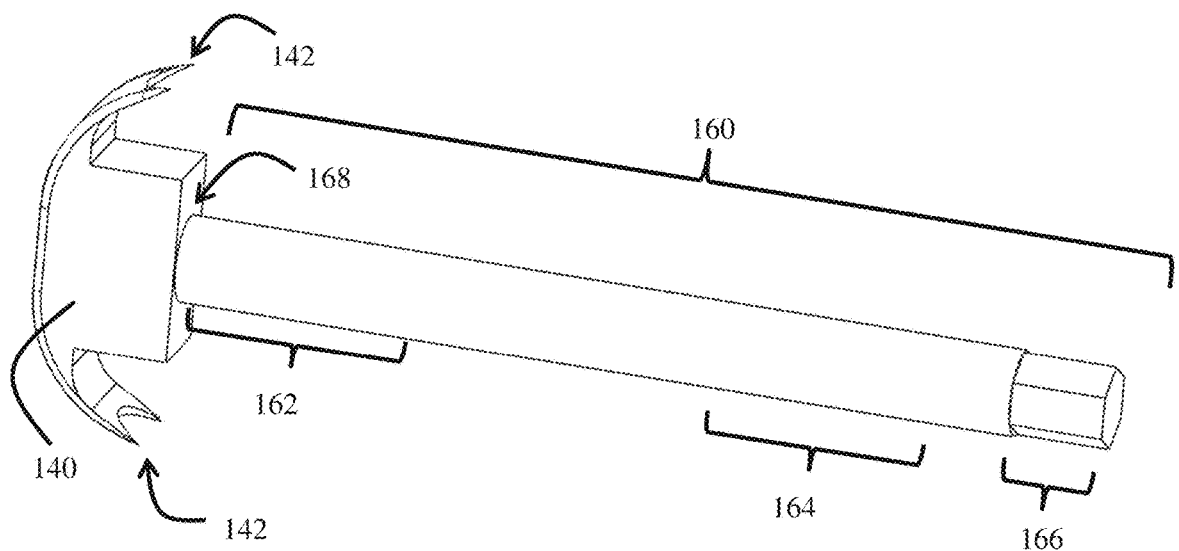

Referring to FIG. 1C, the staple 140 is generally a device coupled to the distal end of the screw 160 to frictionally engage the external surface of the vertebral body to secure one end of the implant device to the body. In the example embodiment shown, the staple 140 has staple tines 142 to function as barbs to secure the implant device 100 to the external surface of the vertebra. The staple 140 and screw 160 are coupled with a swivel coupler 168 which allows some movement of the staple to better accommodate the anatomical shape of the vertebra. The swivel coupler 168 may comprise a screw swivel coupler that mates with a staple swivel coupler. The staple 140 may articulate relative to the screw 160 by means of material deformation or a mechanical joint feature to accommodate anatomical variance. In one example embodiment, the screw 160 is coupled with a swivel coupling that secures the staple 140 on the distal end of the screw 160 but also allows the staple 140 to rotate about the screw 160.

Referring to FIG. 1C, the staple 140 is free to move and rotate on the distal end of the screw 160, but, the swivel coupling of the staple 140 has some friction to allow the staple 140 to rotate when the screw 160 rotates. When the staple 140 is rotated while the implant device is in the vertebral opening of the osteotomy (see FIG. 8C), and the screw 160 is rotated and the staple 140 rotates with it (based on swivel coupling friction) until it hits a stop (overcoming swivel coupling friction) leaving it in the deployed position (see FIG. 8D). Further rotation of the screw 160 draws the staple 140 and the plate 120 together allowing the staple tines 142 and the plate tines 122 to engage the bone of the vertebral body and secure the implant device. In one embodiment, the stop is created by a proximal end of the staple having a radiused corner profile that allows the staple to rotate until the larger radius section engages the internal surface of the vertebral body and stopping further rotation of the staple (see FIG. 2D). In this embodiment, the radiused corner profile of the staple also helps support the opening in the vertebral body.

Referring to FIG. 1C, the screw 160 is generally an elongated member configured to couple the staple 140 with the nut 130 so that all of the implant device components may be coupled together. As shown in FIG. 1C, the screw 160 comprises swivel coupler 168, a distal portion 162, a proximal portion 164 and a drive portion 166. The distal portion 162 and the proximal portion 164 may be threaded (see FIG. 2A). In an embodiment with threaded portions, the externally threaded distal portion 162 is configured to mate and engage an internally threaded portion of the hole in the distal end of the plate 120 and an externally threaded proximal portion 164 is configured to mate and engage an internally threaded portion of an internal bore in the nut 130. In embodiments, the threaded portions of the screw may have the threads configured to work in different directions to allow for different engagement of the screw when the screw is rotated in different directions. For example, the externally threaded distal portion 162 may be threaded with left-handed threading (see. FIG. 2B) to draw the distal end of the screw closer to the distal end of the plate 120 when the screw is turned clockwise and the externally threaded proximal portion 164 may have right-handed external threading (see FIG. 2C) to mate with the internal right-handed threading of the nut to allow the nut to be secured and brought further onto the screw when the nut is turned in the counter-clockwise direction. In this example, the screw is turned/tightened in the body by a drive tool that mates with the drive portion 166 of the screw 160 and the nut is turned/tightened on the screw 160 by a drive tool that mates with the proximal end of the nut.

The threaded portions of the screw may have a locking thread profile to mate and lock with the mating threads. For example, a locking thread profile may be created when tapping the female thread and is created by a sloped surface which taper-locks the apex of the external/male thread. For example, when the screw or nut is tightened, the crests of the male threads on the bolt are pulled up against the sloped surface of the female threads and wedged into place creating a locking thread.

During insertion of the intravertebral implant device, the staple 140 is configured in a horizontal position, generally parallel with transverse surface planes of the plate 120, for ease of insertion. The staple 140 is then configured to be rotated by a rotation of the screw 160 into a vertical/perpendicular position (see FIG. 1G) once it extends beyond the far side of a vertebral body. Once the staple 140 is in the correct position, the staple 140 and plate 120 are then stabilized together. This stabilization may be done by rotating the drive portion 166, such as a hex shaped profile on the proximal end of the screw 160. Generally, this would be done in the same rotational direction as was used to position the staple to ensure the stop engages the vertebra and keeps the staple tines engaged with the vertebral body. By rotating the screw 160 with the drive portion 166 in a clockwise rotation, the screw in the plate draws the staple and plate together, engaging the tines of the staple and the plate into the cortical shell of the vertebral body. This can occur because of staple prongs of the plate capture the ipsilateral vertebra body cortex, as shown in FIGS. 8C-8E and described in methods of using the intravertebral implant device.

The plate generally provides the structure to secure the implant device to both sides of the vertebra. The plate is configured to adjustably couple with the screw and staple to secure the implant device to one side wall of the vertebra and the plate has tines on a proximal end to secure the implant device to the other side wall of the vertebra.

Figure 1D:
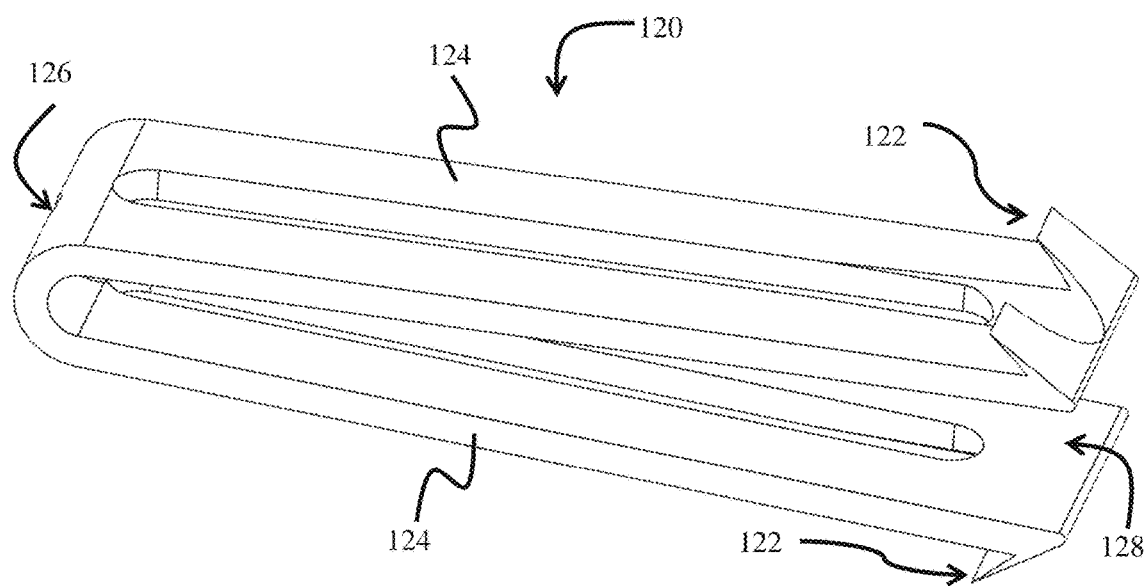

Referring to FIG. 1D, the plate 120 is generally an angularly flexible device with plate tines 122 at the end of prongs 124 to engage the two vertebral body portions superior and inferior to the osteotomy. The plate tines 122 can be made to accommodate anatomical variance. The plate may be a two-pronged u-shaped angularly flexible body defining a cavity 128 configured to receive the wedge and the screw. The cavity 128 may be configured to receive and be used with multiple shapes of wedges. This allows multiple configurations of the intravertebral implant device to be provided by altering the wedge used with the plate 120. The plate also has a through hole 126 at its distal end to receive and engage the distal end of the screw. In some embodiments, the through hole 126 is threaded to mate with the distal threaded portion of the screw. In some embodiments, the threads of the through hole 126 are configured to have a locking profile to lock with the screw threads.

Figure 1E:
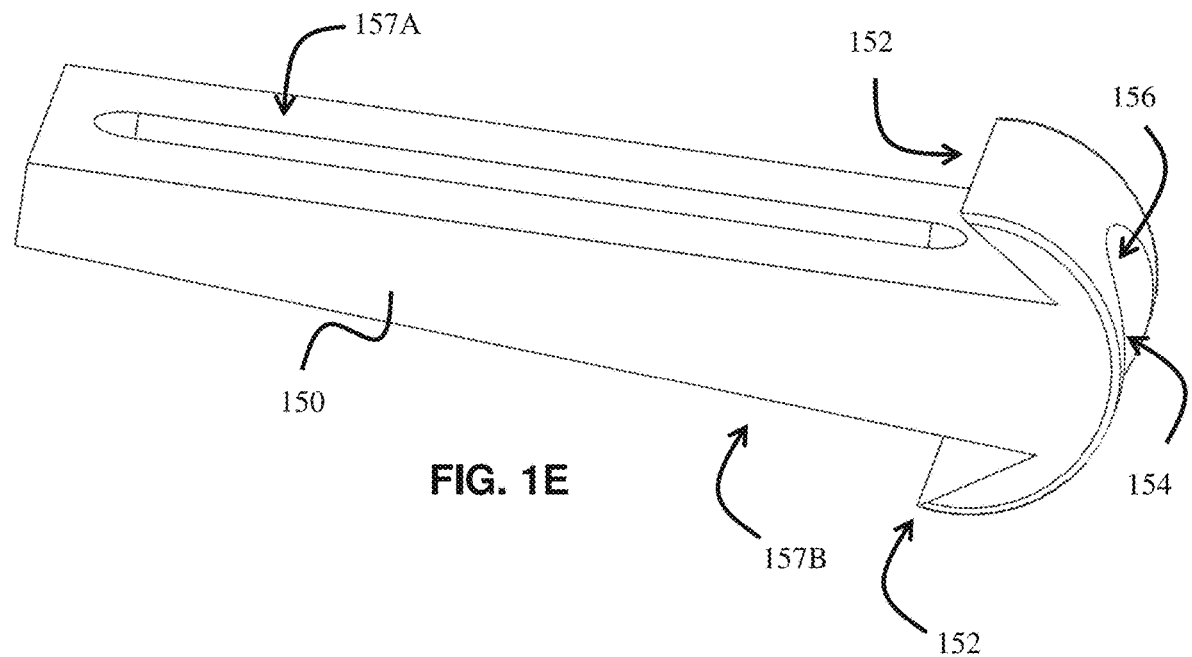

Referring to FIG. 1E, the wedge 150 is generally a triangle shaped element used to distract the plate and influence the external surface configuration of the implant device and effect correction to the vertebral body. The wedge has variable dimension along its longitudinal axis which defines a wedge longitudinal angle between a wedge top surface plane 157A and a wedge bottom surface plane 157B. The wedge 150 may also have variable dimension along its transvers axis to provide a wedge transverse angle between the wedge top surface plane 157A and the wedge bottom surface plane 157B. The wedge 150 is also configured to fit within the cavity of the plate. This allows for multiple configurations of the wedge 150 to be used with a common plate so that the implant device can be configurable.

The wedge tines 152 on the wedge 150 engage the plate tines to prevent them from separating. This resists tensile forces, bending forces and resists the osteotomy from opening further. The wedge tines 152 may also engage the bone to further secure the implant device to the vertebra.

The wedge 150 also has a through bore 154 extending along its length and shaped to receive the screw and the nut. The wedge 150 may also have a concave recess 156 at its proximal end to receive and countersink the head of the nut when the implant device is secured to the vertebra.

Figure 1F:
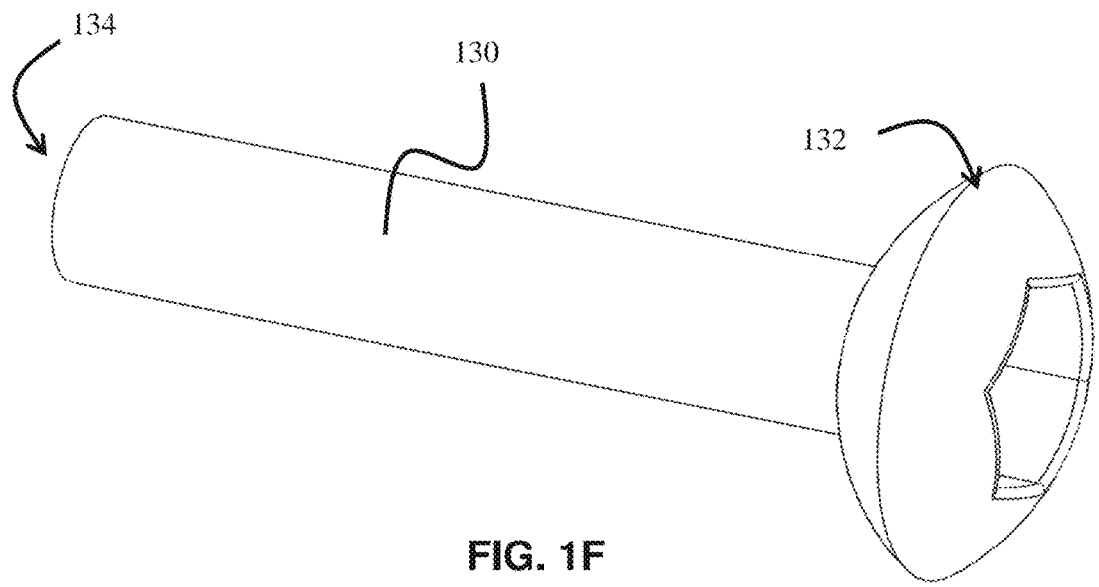

Referring to FIG. 1F, the nut 130 is generally an internally threaded tubular element with a head 132 and is used to engage a mating threaded recess in the wedge draw the wedge into the plate/cage and secure the implant assembly. In the embodiment shown, the nut has a recess 134 with internal threads configured to couple with the external threads of the screw. The recess 134 of the nut is also shaped to receive the drive portion of the screw. In some embodiments, the threads have a locking profile to lock with the mating threads of the screws. In some embodiments, the direction of the threading is opposite to the threading direction of the distal end of the screw. This opposing threading direction is to allow the distal end of the screw to be secured in the plate while also allowing the nut 130 to be secured to the proximal portion of the screw by rotating in a direction that doesn't loosen the engagement of the screw with the plate.

Figure 1G:
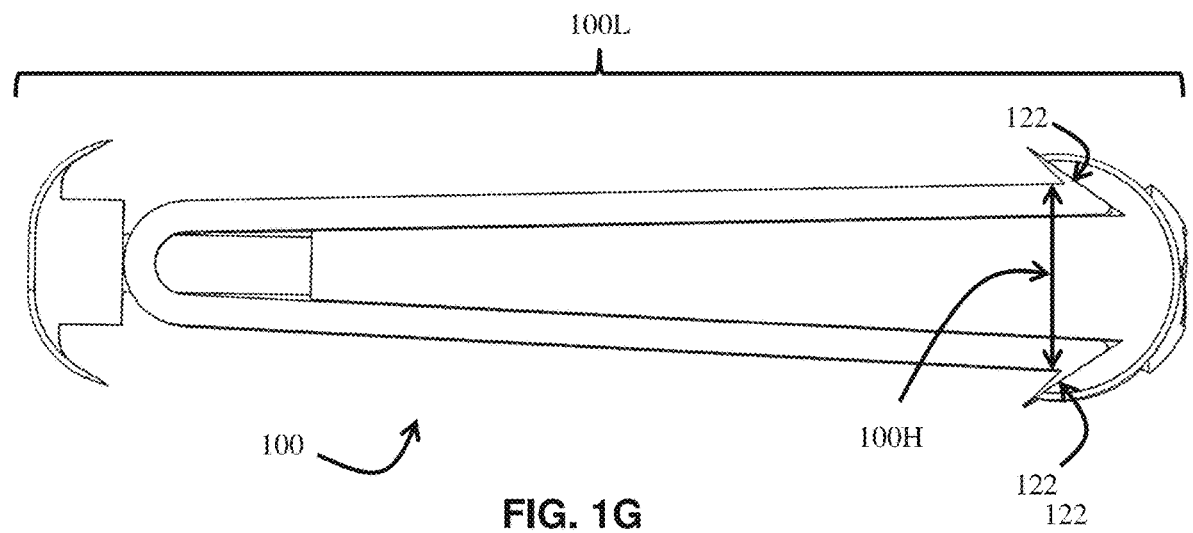

FIG. 1G shows the embodiment of FIG. 1B, as assembled, from a side-view. Shown is the implant device length 100L and the plate height 100H, corresponding to the implant device height as measured at the proximal end of the plate prongs 124 proximal to the plate tines 122.

Figure 1H:
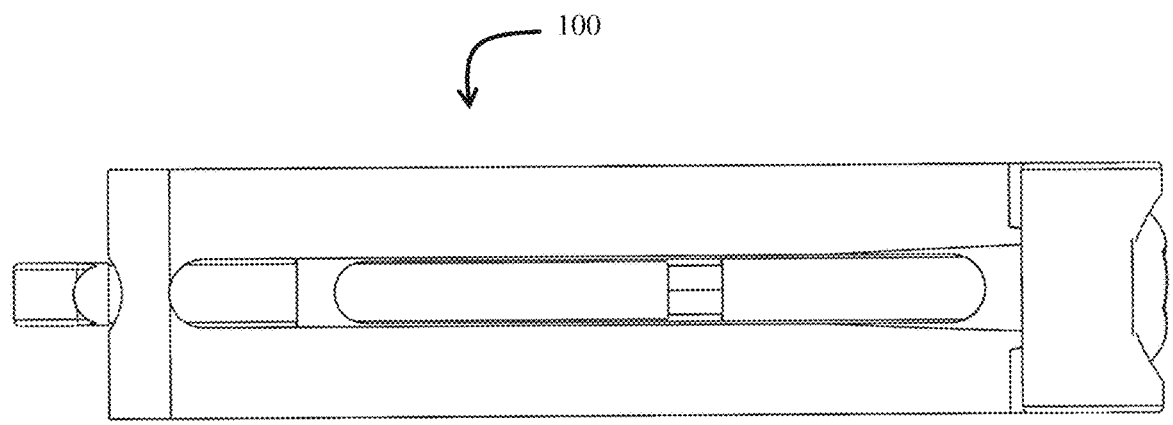

FIG. 1H shows the embodiment of FIG. 1B, as assembled, from a top view.

Figure 1I:
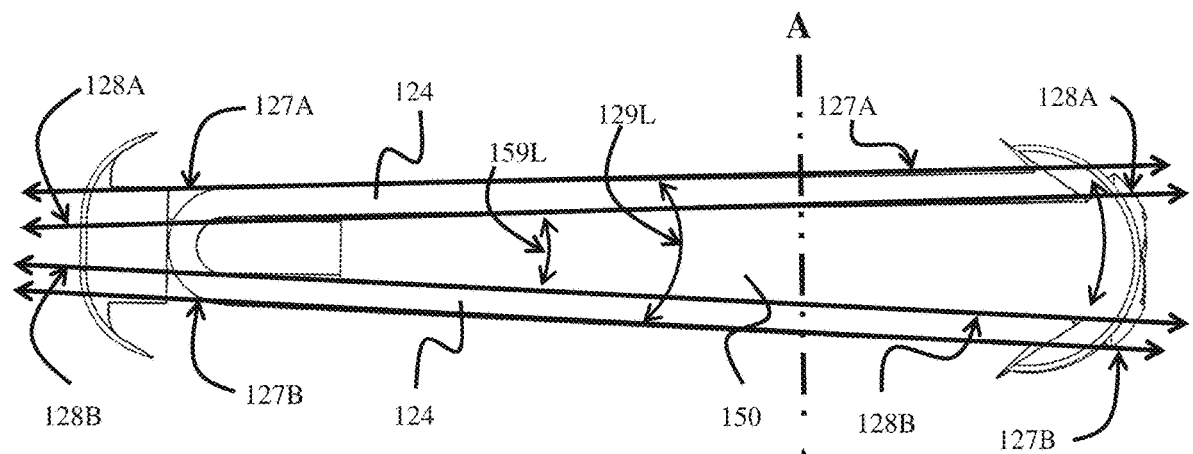

FIG. 1I shows the embodiment of FIG. 1B, as assembled, from a side view illustrating the longitudinal angles between surface planes of implant device components. As shown, the external surface of the prongs 124 define exterior surface planes of the plate and the device. The exterior surface planes extend along the length of the prong 124 and transverse along the width of the prong. Along the length of the plate prongs 124, the exterior surfaces superior and inferior surface) define two exterior surface planes, a top exterior surface plane 127A and a bottom exterior surface plane 127B. Along the length of the plane, the two exterior surface planes define a longitudinal angle 129L between the two longitudinal surface planes 127A and 127B. Similarly, along the length of the wedge 150, the exterior surfaces (superior and inferior surface) of the wedge define two exterior surface planes. These two exterior surface planes define a wedge longitudinal angle 159L between the two surface planes along their length. When assembled, the plate surface planes 127A and 127B cooperate with the dimensions and surface planes of the wedge 150 to create an implant device longitudinal angle, here 129L.

In some embodiments, an additional plate longitudinal angle (not shown) is formed by a change of thickness of the plate prongs along their longitudinal axis creating an angle between the exterior surface planes of the plate prongs and interior surface planes of the plate prongs.

Figure 1J:
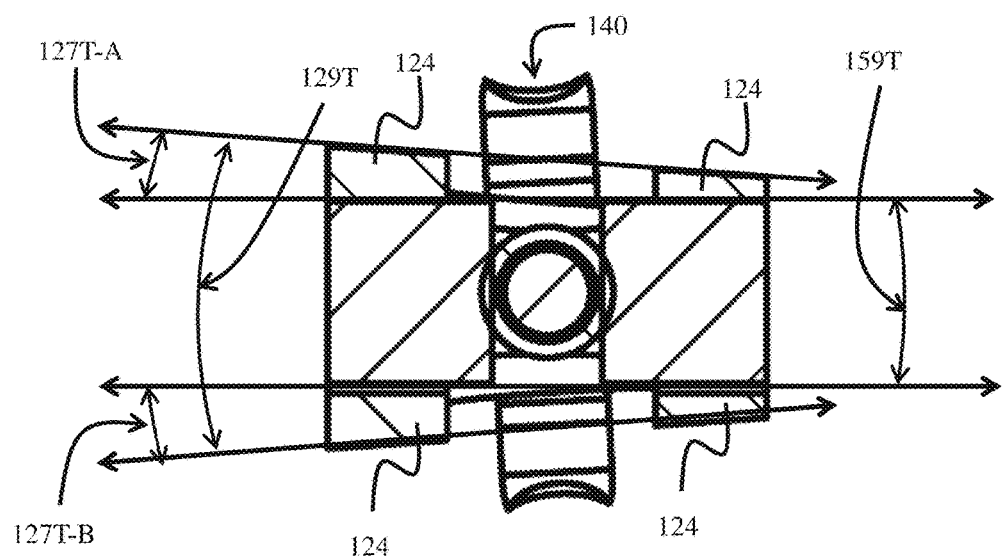

FIG. 1J shows the embodiment of FIG. 1I, as assembled, from a cut-away view A-A illustrating possible transverse angles of implant device components. As shown, a wedge transverse exterior surface plane angle 159T (of the exterior surface planes) is defined by the angular relationship of the transverse surface planes of the wedge. An implant device transverse exterior surface plane angle 129T (of the device/plate exterior surface planes) defines the resulting transverse angle of the outer surface planes of the plate in the transverse direction. The plate transverse exterior surface plane angles 127T-A and 127T-B (of the plate exterior surface planes) are formed by the thickness of the plate prongs 124 along the transverse axis and defines the transverse angle of the outer surface plans of the plate prongs 124.

Figure 1K:
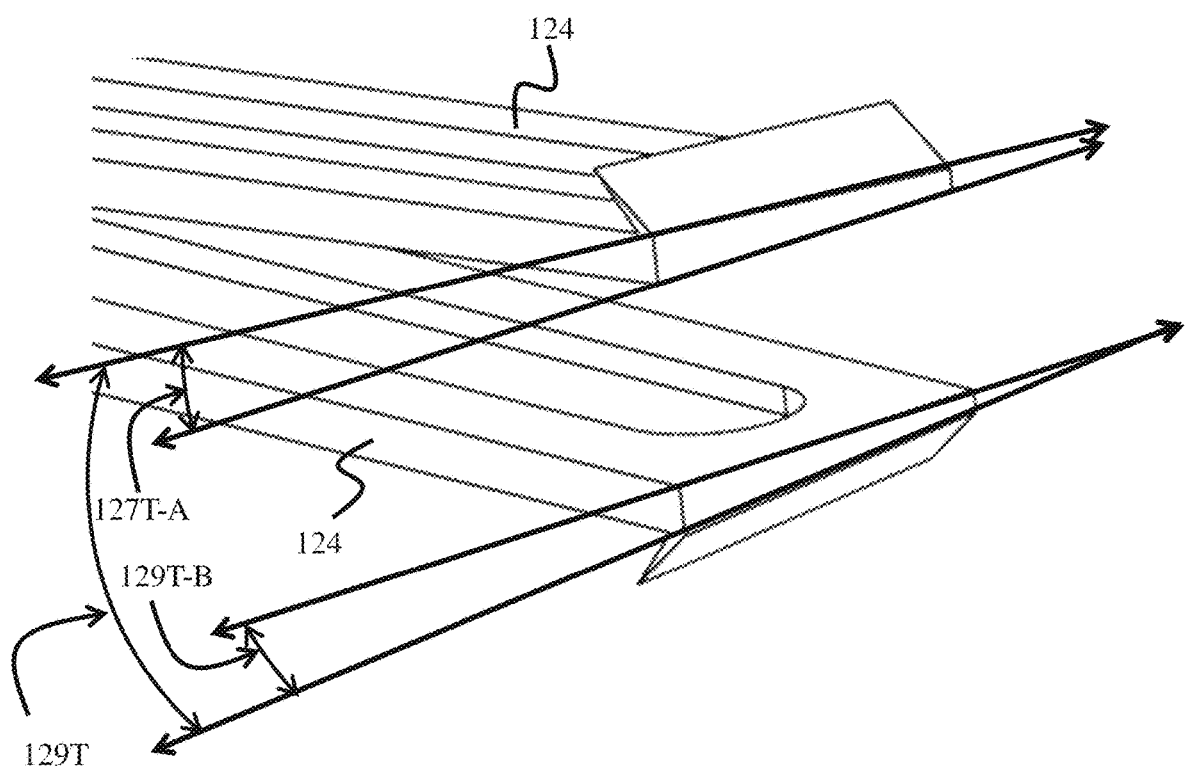

FIG. 1K shows a plate illustrating an example of transverse angles of the plate prongs 124 resulting from a change in the plate thickness in a transverse direction. FIG. 1K shows an example of the plate transverse exterior surface plane angles 127T-A and 127T-B defined by the different orientations of the plate surface planes of the prongs 124 to create the implant device transverse exterior surface plane angle 129T. The plate thickness may be varied to create these angles.

Figure 2E:
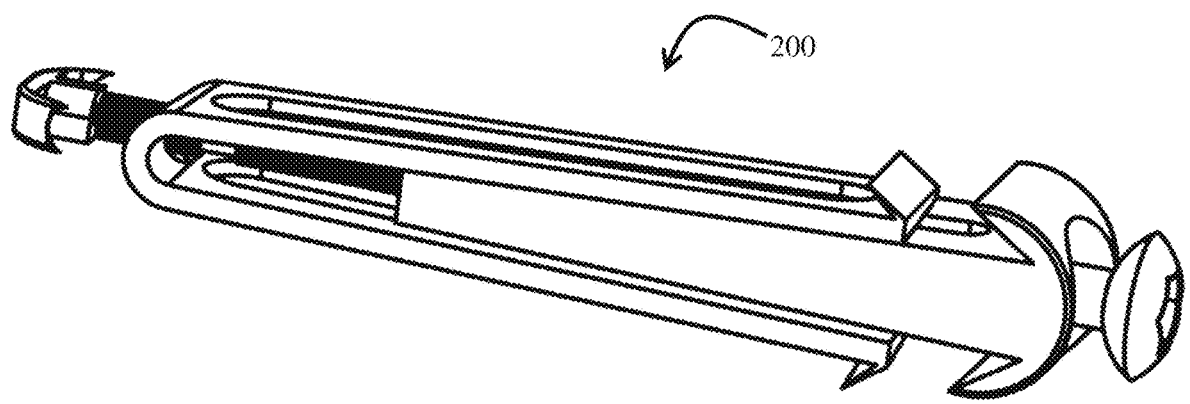
Figure 2F:
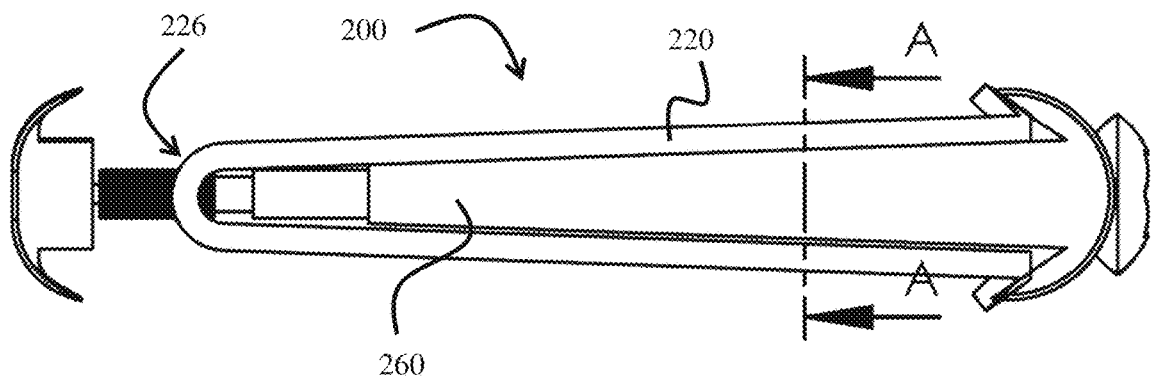
Figure 2G:
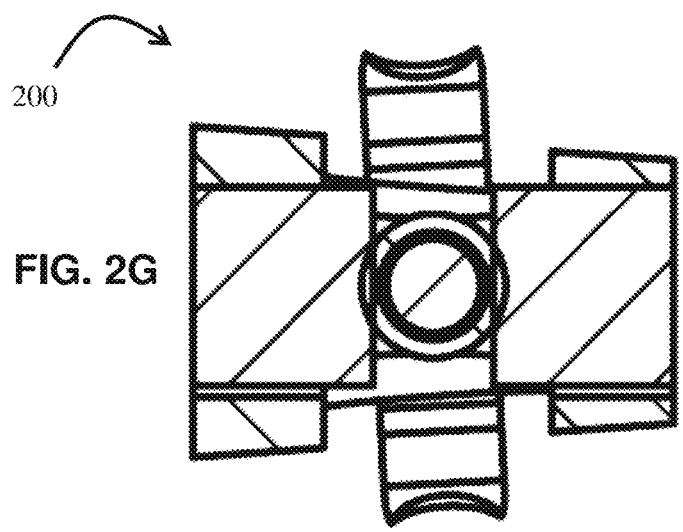
Figure 2H:
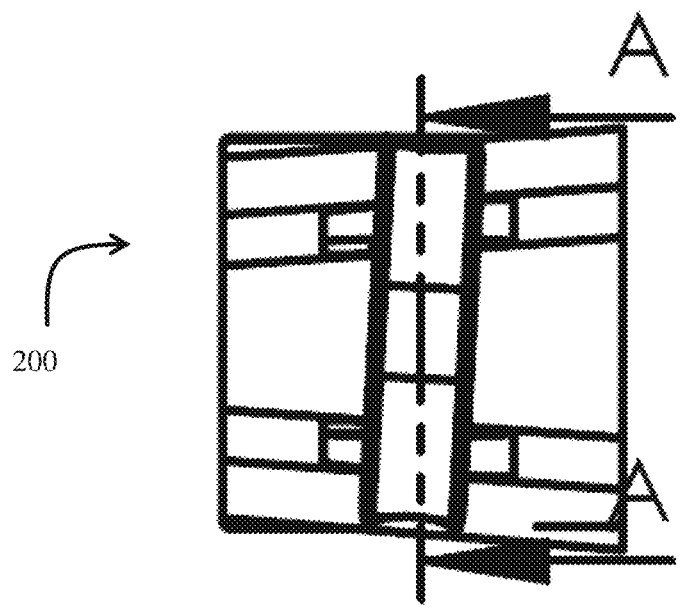
Figure 2I:
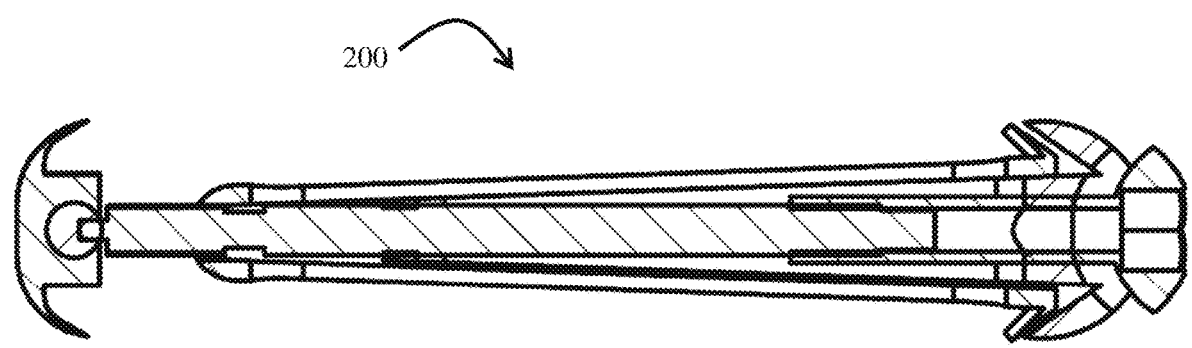

FIGS. 2A-2I show example embodiments detailing features of the intravertebral implant device. As shown in FIGS. 2A-2C, the distal portion 262 of the screw 160 is threaded in a first direction (see FIG. 2B) and the proximal portion 264 of the screw 260 is threaded in an opposite direction (see FIG. 2C). As shown in FIGS. 2E and 2F, the threads of the distal portion 262 of the screw engage the hole in the distal end of the plate 220. FIG. 2E shows a perspective view of the implant device with the distal threaded portion of the screw. FIGS. 2F and 2G show a side view and cross-sectional view of the implant device. FIG. 2H shows a view of the implant device from a distal end showing an implant device with transverse angles on the wedge. FIG. 2I shows a cross-sectional view of the implant device along the cross-section A-A of FIG. 2H which is a cross-section along the length of the implant device.

Consistent with the screw 260 embodiments shown in FIGS. 2A-2C, FIG. 2D illustrates an example embodiment of the radiused corner profile on the proximal end of the staple 240. In one embodiment, the stop is created by a proximal end of the staple having a radiused corner profile with a rounded profile section 244 that creates a smaller radius about the screw and a larger profile section 246 that creates a larger radius about the screw. This profile allows the staple to rotate until the larger profile section engages the internal surface of the vertebral body and stops further rotation of the staple.

Configurable Features of Embodiments of the Intravertebral Implant System:

The ability to mix plate components and wedge components allows for multiple implant device dimensions to be created so that different alterations can be made to the alignment of the spine. These different implant device dimensions can be made to be suitable to support insertion from different angles and use in different regions of the spine. In addition, devices sizes may vary for use with different patients.

As shown in the examples of Table A of FIG. 6, many different configurations of the implant device may be created. Use of the implant device may be used to create a wedged vertebrae correction (WVC) or a foraminal stenosis correction (FSC).

Examples of general sizes of the implant device are also shown in Table A of FIG. 6. Final sizes for the vertebral implant device in length, width and height are generally based on dimensions of human vertebrae. Configurations of the vertebral implant device angles, longitudinal and transverse, are selected based on the correction desired in the sagittal and coronal plane. The vertebral implant device dimensions are a result of the dimensions of wedge and the plate. Limits of correction angles will be formulated using Finite Element Analysis (FEA) and design analysis based on anatomical ranges.

Examples of sizes and configurations for the vertebral implant device are illustrated in the following description of embodiments in operation.

Figure 3:
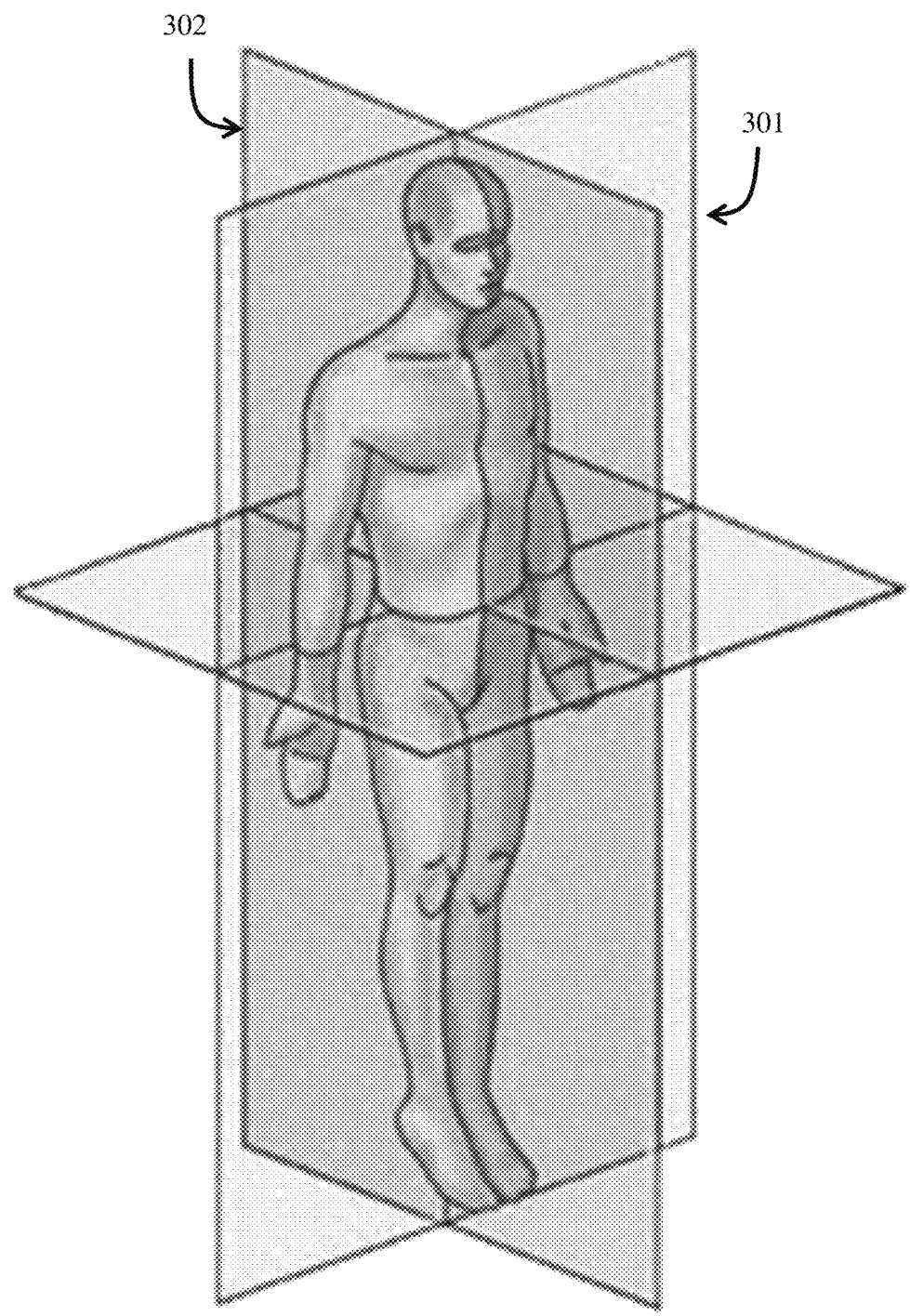
FIG. 3 shows the planes of the human body.

One Embodiment of the Intravertebral Implant System in Operation:

The vertebral implant device generally uses the exterior surface planes of the implant device to alter the alignment of skeletal components of a mammalian body. Referring to FIG. 3, the disclosed vertebral implant device primarily provides adjustment of the spine in the coronal plane 301 and the sagittal plane 302 and combinations of the two planes.

Figure 4:
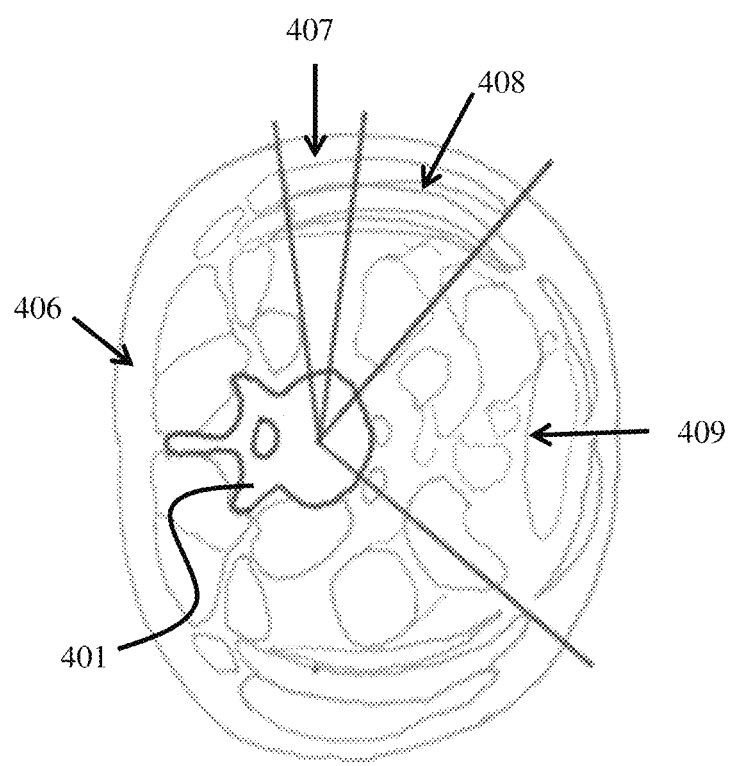
FIG. 4 shows a lateral plane section of the human body at mid-lumbar level.

Referring to FIG. 4 showing a cross-section of the human body, the vertebral implant device is intended to be used on the vertebra 401 of a body 406 and may be inserted from different orientations. As shown, the implant device may be inserted from a lateral position 407, from an anterior position 409 or from an oblique position 408. The intravertebral implant system may also be applied to different portions of the spine.

Figure 5A:
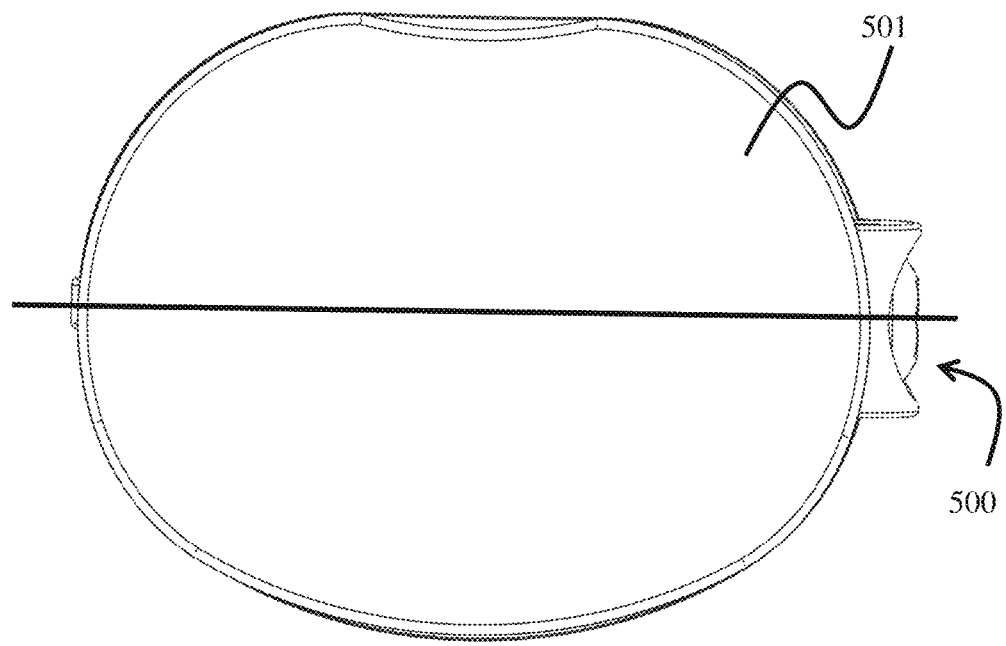
FIGS. 5A-5C shows example embodiments of the intravertebral implant device inserted from different insertion angles where
Figure 5B:
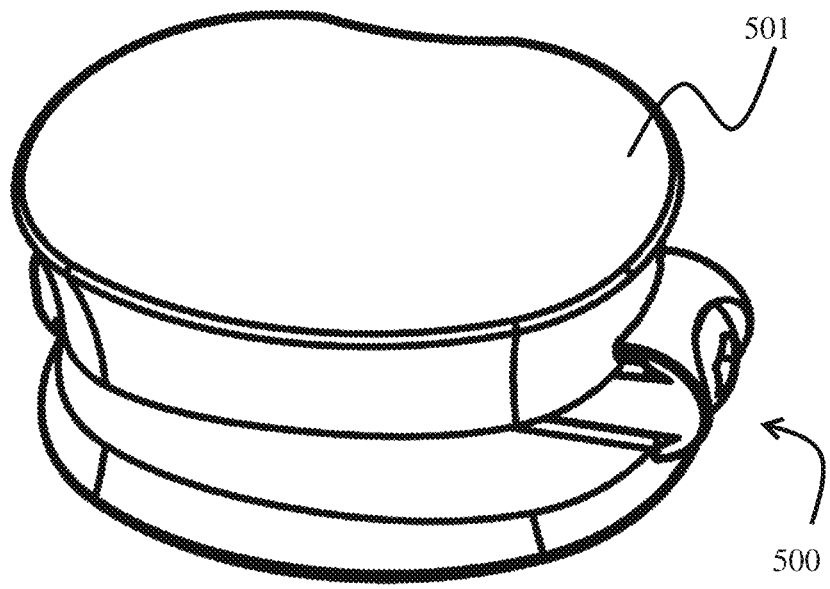
Figure 5C:
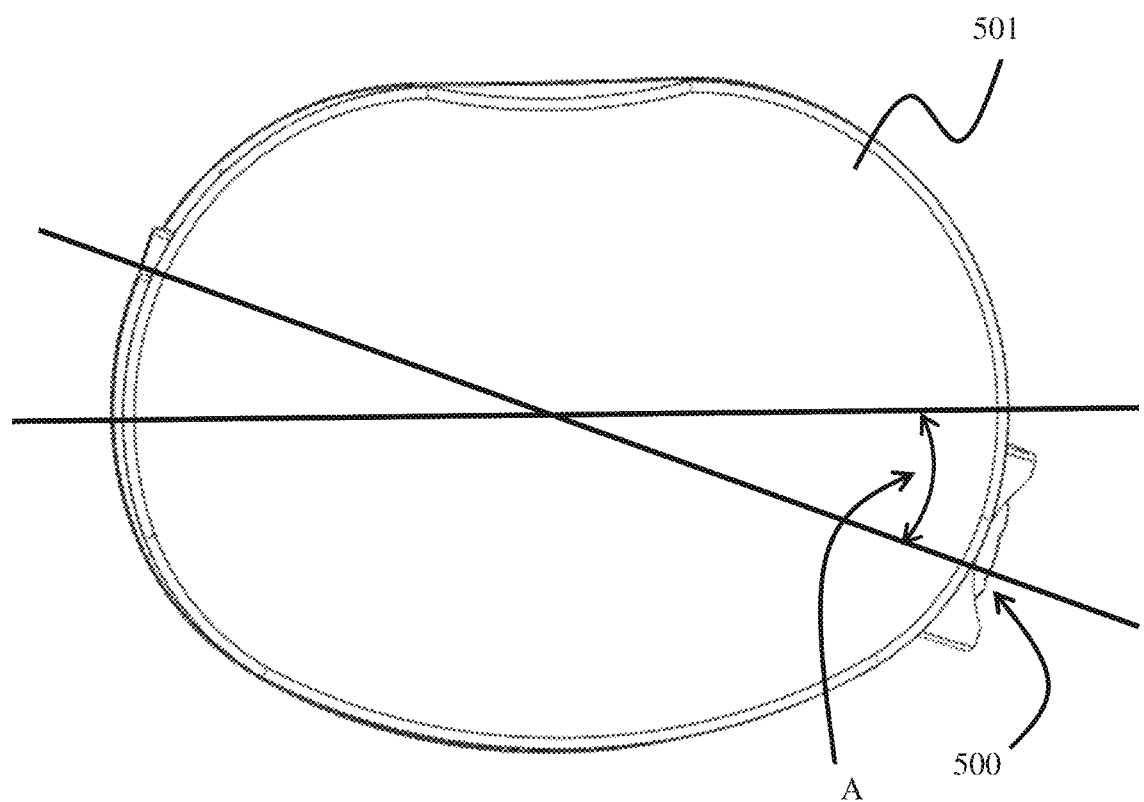

FIGS. 5A-5C further illustrate the ability for multiple embodiments of the vertebral implant device to be inserted. FIG. 5A shows a top view of an example embodiment of an intravertebral implant device 500 inserted in a vertebra 501 from a lateral approach with the longitudinal axis of the implant device generally in the coronal plane. FIG. 5B shows a top perspective view of an intravertebral implant device 500 inserted in a vertebra 501 from a lateral approach. FIG. 5C shows a top view of an example embodiment an intravertebral implant device 500 inserted in a vertebra 501 from an oblique approach at an angle A from a normal lateral approach.

Described below in detail is a lateral approach for creating a vertebral body osteotomy and then for placing the implant totally within the vertebral body for correction in the coronal plane. With the disclosed systems and methods, spine correction is established, while the spine flexibility thru the disc and facet joints is retained, and the vertebral body then fuses in a period of time, such as 12 weeks, for a solid corrected vertebral structure.

Referring to FIGS. 8A-8G, the operation of one embodiment of the intravertebral implant system generally comprises the following sequence of steps.

Figure 8A:
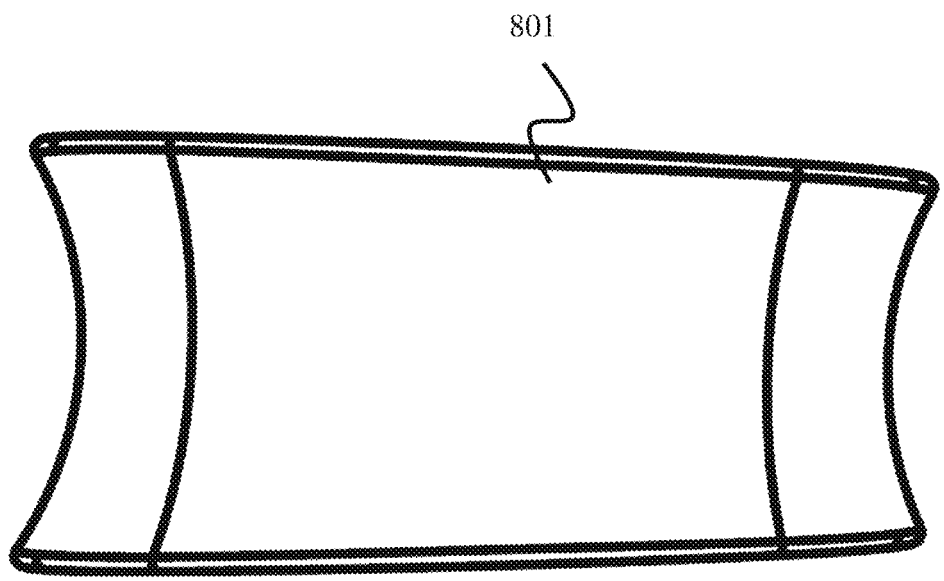
FIGS. 8A-8G illustrate example methods of inserting the an intravertebral implant device.
Figure 8B:
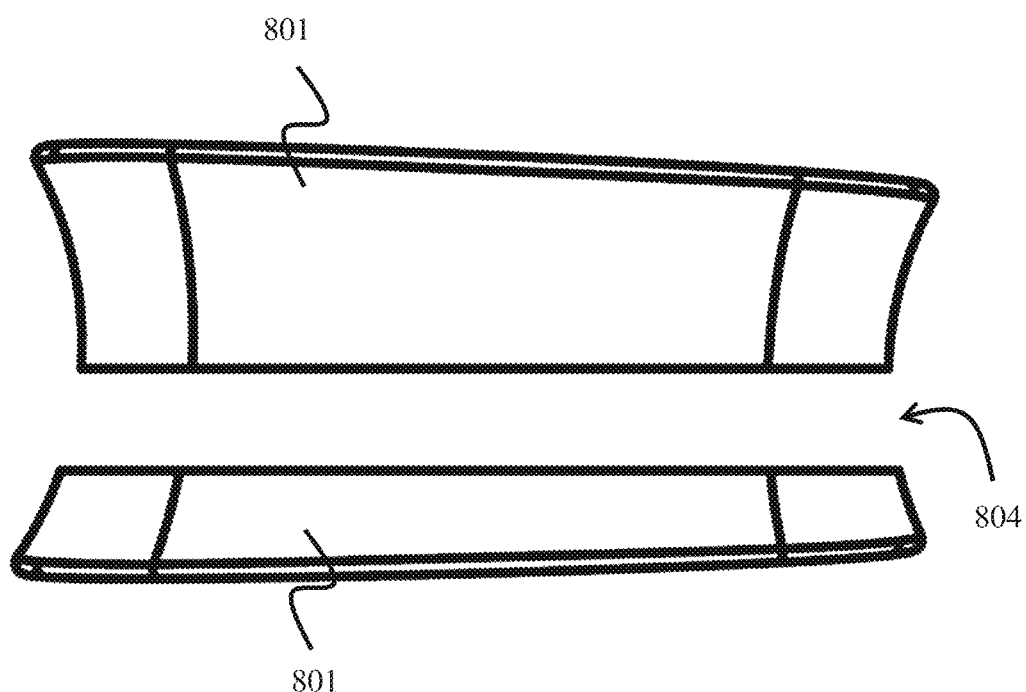
Figure 8C:
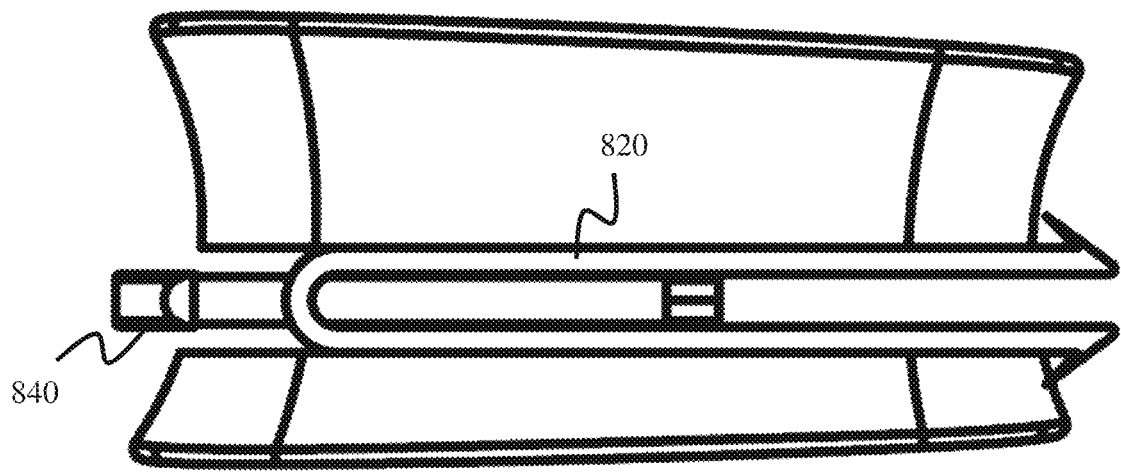
Figure 8D:
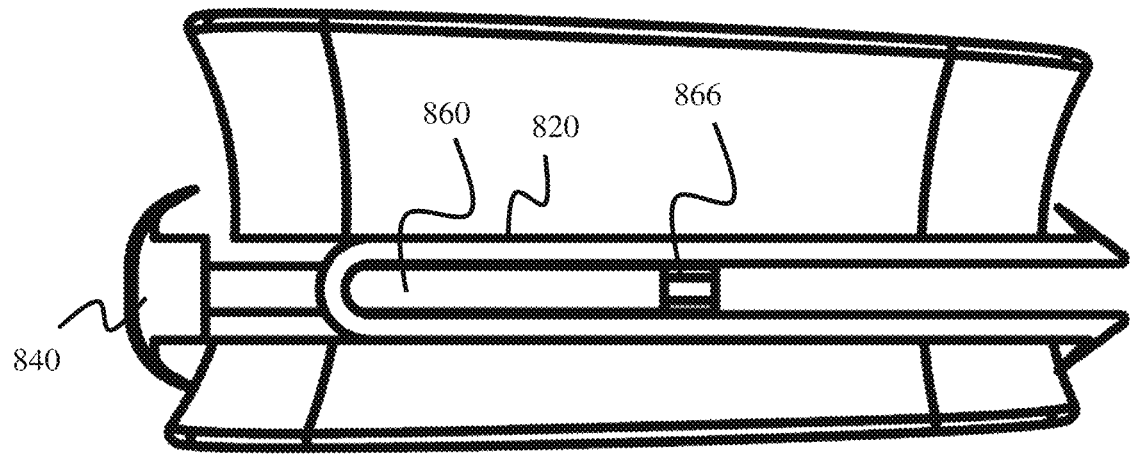
Figure 8E:
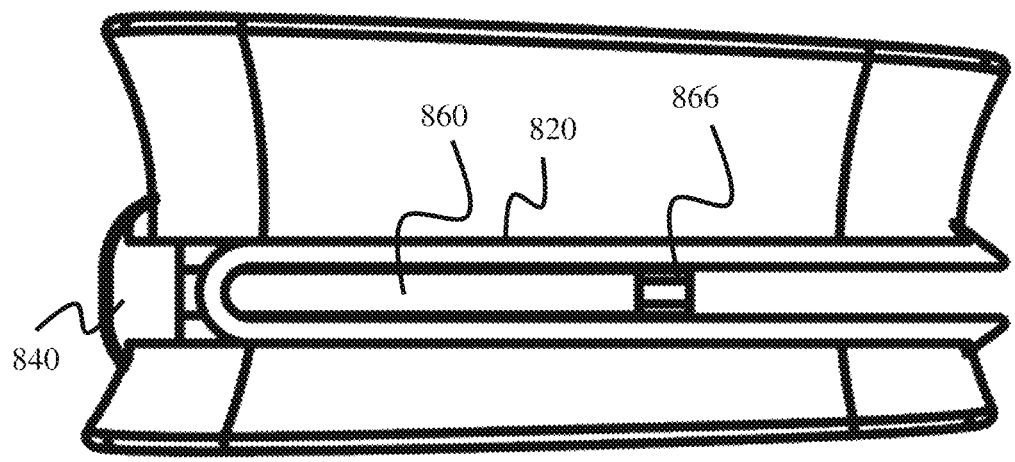

As shown in FIGS. 8A and 8B, an osteotomy 804 is made through the vertebral body 801 from the concave side and inferior to the inferior aspect of the pedicle.

As shown in FIG. 8C, a plate 820 with staple 840 is inserted into the osteotomy. As shown, the staple 840 is in an inserted orientation to pass through the osteotomy.

As shown in FIG. 8D, the staple 840 rotated with the screw 860 to engage the far side vertebra cortex wall. The staple 840 is rotated in a first direction by having a drive tool engage the drive portion 866 of the screw 860. With rotation, the staple 840 is stopped by the radiused corner profile of the staple proximal end.

Referring to FIG. 8E, with the staple 840 inserted and stopped, the staple 840 and plate 820 are tightened by rotating the drive portion 866 further in the first direction to draw the screw 860 and staple 840 towards the plate 820. Rotating the screw 860 engages all the staple tines into the side wall of the vertebral body as well as draws the plate tines into the opposing side wall of the vertebral body. With the staple tines and plate tines engaged with the vertebral body, the implant device is secured to the vertebral body.

Figure 8F:
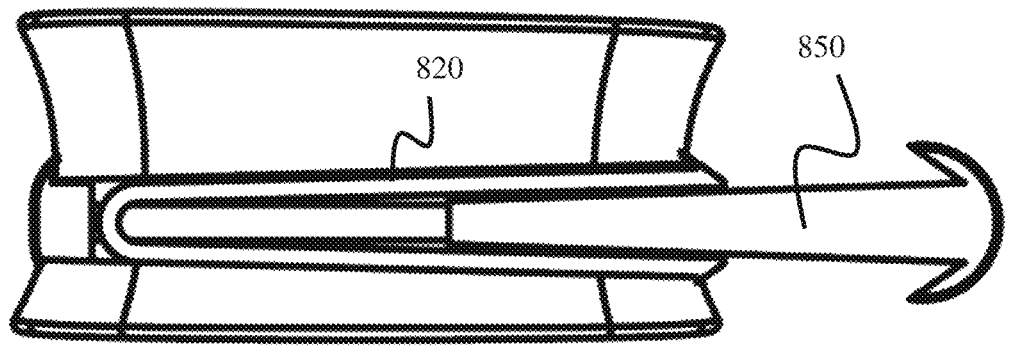

Referring to FIG. 8F, the wedge 850 is then inserted into the cavity of the plate 820 and the nut (not shown) is coupled to the proximal threaded portion of the screw. With the tightening of the nut to draw the nut onto the screw 860 (using the right-hand threads on the screw) the wedge 850 slides into the cavity, distracting the plate 820, distracting the exterior surface planes of the implant and correcting the vertebral body coronal angle.

Figure 8G:
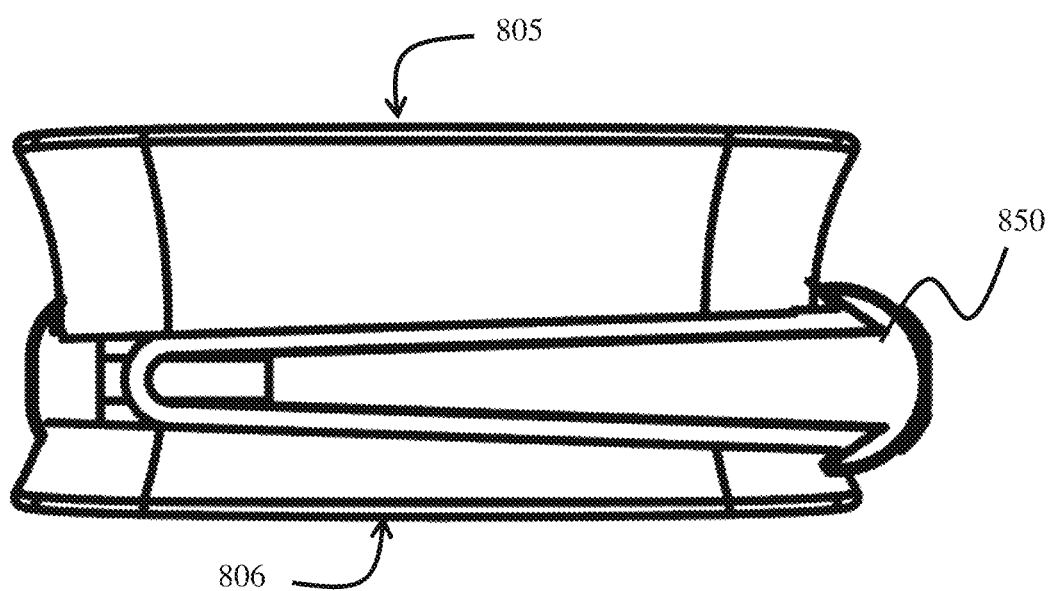

Referring to FIG. 8G, the wedge 850 is then secured into position by a tightening of the nut. When the wedge 850 is fully in place, it engages the plate 820 providing a solid construct. The securing of the wedge 850 creates the correction and the wedge tines engage the plate tines and secures the upper and lower prongs of the plate 820 together. The result is an alteration of the relative orientation of a superior endplate surface plane 805 and an inferior endplate surface plane 806 of the vertebral body to alter the alignment of the spine.

For safety purposes, locking thread profiles may be provided on internal machine screw threads of the hole in the plate and the internal threads of the nut to prevent loosening or disengagement of the vertebral implant device once it is implanted.

In some embodiments, the vertebral implant device may provide additional correction in the sagittal plane. In these embodiments, the wedge surfaces will have a single angle and the inside of the plate will have a single angle and there will be transverse angles on the outside of the plate. This transverse angle of the plate additionally provides some correction in the sagittal plane and when implanted from a lateral approach.

In some embodiments, the vertebral implant device may be inserted from other approaches or may be used to alter alignment in other planes. With other approaches, the general method of inserting and securing the implant device is similar to the methods above. The different approach direction will require different configurations of the implant device so that the exterior surface planes provide the desired alteration in superior endplate surface plane and the inferior endplate surface plane of the vertebra in the appropriate plane.

Example Embodiments of Implant Devices to be Used with Lateral Insertion:

Example embodiments of intravertebral implant devices suitable for insertion from a lateral approach will be described below. Because the implant device is configurable, many of the implant device components are the same; the difference is in selecting different sized components to suit the direction of insertion, the spinal plane to be corrected and the area of the spine to be corrected. The descriptions below utilize an implant device consistent with the embodiments described above and shown in FIGS. 2A and 2E. The descriptions below will utilize the dimensional examples shown in Table A of FIG. 6. It is understood that although Table A identifies dimensions and angles in logical increments, these increments are illustrative only of values within a range encompassing those values.

Lateral Insertion to Adjust Coronal Alignment

One example embodiment of an intravertebral implant device suitable for insertion from a lateral approach to correct vertebral alignment in the coronal plane is described above and shown in FIGS. 2A and 2E.

For insertion from the lateral direction to correct spinal alignment in the coronal plane, an intravertebral implant device will be selected that has a suitable implant device longitudinal angle. In most embodiments, this implant device longitudinal angle is dictated by the wedge longitudinal angle. For example, referring to Table A in FIG. 6, for a lateral insertion to correct a lumbar area vertebra in the coronal plane, an implant device can be selected that has a wedge longitudinal angle in the range of about 5-20 degrees which will provide an overall alignment effect in the coronal plane of about 5-20 degrees. In some embodiments, the implant device and wedge longitudinal angle is in the range of about 10-15 degrees and in some embodiments, the implant device and wedge longitudinal angle is about 10 degrees.

For use in the thoracic area, the intravertebral implant device will be similarly configured but will generally have smaller dimensions. For example, referring to Table A in FIG. 6, for a lateral insertion to correct a thoracic area vertebra in the coronal plane, an implant device can be selected that has a wedge longitudinal angle in the range of about 5-15 degrees which will provide an overall alignment effect in the coronal plane of about 5-15 degrees. In some embodiments, the implant device and wedge longitudinal angle is in the range of about 10-15 degrees and in some embodiments, the implant device and wedge longitudinal angle is about 10 degrees.

It is understood, that if additional alignment correction is desired in the sagittal plane, the intravertebral implant device may be selected with implant device transverse angles to provide this correction. This implant device transverse angle may be provided by either a plate transverse angle or a wedge transverse angle. For example, referring to Table A in FIG. 6 and utilizing the plate to provide the implant device transverse angle, for a lateral insertion to correct a lumbar area vertebra in the sagittal plane, an implant device can be selected that has a plate transverse angle in the range of about 1-20 degrees which will provide an overall alignment effect in the sagittal plane of about 1-20 degrees. In some embodiments, the implant device and plate transverse angle is in the range of about 10-15 degrees and in some embodiments, the implant device and plate transverse angle is about 10 degrees. Similarly, referring to Table A in FIG. 6, for a lateral insertion to provide additional correction for a thoracic area vertebra in the sagittal plane, an implant device can be selected that has a plate transverse angle in the range of about 1-10 degrees which will provide an overall alignment effect in the sagittal plane of about 1-10 degrees. In some embodiments, the implant device and plate transverse angle is in the range of about 5-10 degrees and in some embodiments, the implant device and plate transverse angle is about 5 degrees.

Lateral Insertion to Adjust Sagittal Plane Alignment

One example embodiment of an intravertebral implant device suitable for insertion from a lateral approach to correct vertebral alignment in the sagittal plane is described above and shown in FIGS. 2A and 2E.

For insertion from the lateral direction to correct spinal alignment in the sagittal plane, an intravertebral implant device will be used that has a suitable implant device transverse angle. In most embodiments, this implant device transverse angle is dictated by the plate transverse angle. For example, referring to Table A in FIG. 6, for a lateral insertion to correct a lumbar area vertebra in the sagittal plane, an implant device can be selected that has a plate transverse angle in the range of about 1-20 degrees which will provide an overall alignment effect in the sagittal plane of about 1-20 degrees. In some embodiments, the implant device and plate transverse angle is in the range of about 5-15 degrees and in some embodiments, the implant device and plate transverse angle is about 10 degrees.

For use in the thoracic area, the intravertebral implant device will be similarly configured but will generally have smaller dimensions. For example, referring to Table A in FIG. 6, for a lateral insertion to correct a thoracic area vertebra in the sagittal plane, an implant device can be selected that has a plate transverse angle in the range of about 1-10 degrees which will provide an overall alignment effect in the sagittal plane of about 1-10 degrees. In some embodiments, the implant device and plate transverse angle is in the range of about 5-10 degrees and in some embodiments, the implant device and plate transverse angle is about 10 degrees.

It is understood that although the above example shows the implant device transverse angle being provided by the plate transverse angle, a wedge transverse angle, or a combination of the wedge transverse angle and the plate transverse angle may provide the device transverse angle.

It is understood, that if additional alignment correction is desired in the coronal plane, the intravertebral implant device may be selected with implant device longitudinal angles to provide this additional correction. As described above for correction in the coronal plane, the implant device longitudinal angle may be provided by either a plate longitudinal angle or a wedge longitudinal angle or a combination of the them. For example, referring to Table A in FIG. 6 and utilizing the wedge to provide the device longitudinal angle, for a lateral insertion to provide additional correction for a lumbar area vertebra in the coronal plane, an implant device can be selected that has a wedge longitudinal angle in the range of about 5-20 degrees which will provide an overall alignment effect in the coronal plane of about 5-20 degrees. In some embodiments, the implant device and wedge longitudinal angle is in the range of about 10-15 degrees and in some embodiments, the implant device and wedge longitudinal angle is about 10 degrees. Similarly, referring to Table A in FIG. 6, for a lateral insertion to provide additional correction for a thoracic area vertebra in the coronal plane, an implant device can be selected that has a wedge longitudinal angle in the range of about 5-15 degrees which will provide an overall alignment effect in the sagittal plane of about 5-15 degrees. In some embodiments, the implant device and wedge longitudinal angle is in the range of about 10-15 degrees and in some embodiments, the implant device and plate transverse angle is about 10 degrees.

Example Embodiments of Implant Devices to be Used with Anterior Insertion:

Example embodiments of intravertebral implant devices suitable for insertion from an anterior approach will be described below. Similar to the devices embodiments described above for lateral insertion, the difference in the devices used is in selecting different sized components to suit the direction of insertion, the spinal plane to be corrected and the area of the spine to be corrected. The descriptions below utilize an implant device consistent with the embodiments described above and shown in FIGS. 2A and 2E. The descriptions below will utilize the dimensional examples shown in Table A of FIG. 6.

Anterior Insertion to Adjust Coronal Plane Alignment

One example embodiment of an intravertebral implant device suitable for insertion from an anterior approach to correct vertebral alignment in the coronal plane is described above and shown in FIGS. 2A and 2E.

For insertion from the anterior direction to correct spinal alignment in the coronal plane, an intravertebral implant device will be used that has a suitable implant device transverse angle. This device transverse angle may be provided by either a plate transverse angle or a wedge transverse angle. For example, referring to Table A in FIG. 6 and utilizing the plate to provide the device transverse angle, for a anterior insertion to correct a lumbar area vertebra in the coronal plane, an implant device can be selected that has a plate transverse angle in the range of about 1-20 degrees which will provide an overall alignment effect in the coronal plane of about 1-20 degrees. In some embodiments, the implant device and plate transverse angle is in the range of about 5-15 degrees and in some embodiments, the implant device and plate transverse angle is about 10 degrees.

For use in the thoracic area, the intravertebral implant device will be similarly configured but will generally have smaller dimensions. For example, referring to Table A in FIG. 6, for an anterior insertion to provide correction for a thoracic area vertebra in the coronal plane, an implant device can be selected that has a plate transverse angle in the range of about 1-10 degrees which will provide an overall alignment effect in the coronal plane of about 1-10 degrees. In some embodiments, the implant device and plate transverse angle is in the range of about 5-10 degrees and in some embodiments, the implant device and plate transverse angle is about 5 degrees.

Similarly, for use in the cervical area, the intravertebral implant device will be similarly configured but will generally have smaller dimensions. For example, referring to Table A in FIG. 6, for an anterior insertion to provide correction for a cervical area vertebra in the coronal plane, an implant device can be selected that has a plate transverse angle in the range of about 1-5 degrees which will provide an overall alignment effect in the coronal plane of about 1-5 degrees. In some embodiments, the implant device and plate transverse angle is in the range of about 2.5-5 degrees and in some embodiments, the implant device and plate transverse angle is about 2.5 degrees.

It is understood, that if additional alignment correction is desired in the sagittal plane from this angle of insertion, the intravertebral implant device may be selected with implant device longitudinal angles to provide this correction. This implant device longitudinal angle may be provided by either a plate longitudinal angle or a wedge longitudinal angle. In most embodiments, this implant device longitudinal angle is provided by the wedge longitudinal angle. For example, referring to Table A in FIG. 6, for an anterior insertion to correct a lumbar area vertebra in the sagittal plane, an implant device can be selected that has a wedge longitudinal angle in the range of about 5-20 degrees which will provide an overall alignment effect in the sagittal plane of about 5-20 degrees. In some embodiments, the implant device and wedge longitudinal angle is in the range of about 10-15 degrees and in some embodiments, the implant device and wedge longitudinal angle is about 10 degrees. Similarly, referring to Table A in FIG. 6, for an anterior insertion to also correct a thoracic area vertebra in the sagittal plane, an implant device can be selected that has a wedge longitudinal angle in the range of about 5-15 degrees which will provide an overall alignment effect in the sagittal plane of about 5-15 degrees. In some embodiments, the implant device and wedge longitudinal angle is in the range of about 10-15 degrees and in some embodiments, the implant device and wedge longitudinal angle is about 10 degrees. Similarly, referring to Table A in FIG. 6, for an anterior insertion to also correct a cervical area vertebra in the sagittal plane, an implant device can be selected that has a wedge longitudinal angle in the range of about 2.5-7.5 degrees which will provide an overall alignment effect in the sagittal plane of about 2.5-7.5 degrees. In some embodiments, the implant device and wedge longitudinal angle is in the range of about 5-7.5 degrees and in some embodiments, the implant device and wedge longitudinal angle is about 5 degrees.

Anterior Insertion to Adjust Sagittal Plane Alignment

One example embodiment of an intravertebral implant device suitable for insertion from an anterior approach to correct vertebral alignment in the sagittal plane is described above and shown in FIGS. 2A and 2E.

For insertion from the anterior direction to correct spinal alignment in the sagittal plane, an intravertebral implant device will be used that has a suitable implant device longitudinal angle. In most embodiments, this implant device longitudinal angle is provided by the wedge longitudinal angle. For example, referring to Table A in FIG. 6, for an anterior insertion to correct a lumbar area vertebra in the sagittal plane, an implant device can be selected that has a wedge longitudinal angle in the range of about 5-20 degrees which will provide an overall alignment effect in the sagittal plane of about 5-20 degrees. In some embodiments, the implant device and wedge longitudinal angle is in the range of about 10-15 degrees and in some embodiments, the implant device and wedge longitudinal angle is about 10 degrees.

For use in the thoracic area, the intravertebral implant device will be similarly configured but will generally have smaller dimensions. For example, referring to Table A in FIG. 6, for an anterior insertion to correct a thoracic area vertebra in the sagittal plane, an implant device can be selected that has a wedge longitudinal angle in the range of about 5-15 degrees which will provide an overall alignment effect in the sagittal plane of about 5-15 degrees. In some embodiments, the implant device and wedge longitudinal angle is in the range of about 10-15 degrees and in some embodiments, the implant device and wedge longitudinal angle is about 10 degrees.

Similarly, for use in the cervical area, the intravertebral implant device will be similarly configured but will generally have smaller dimensions. For example, referring to Table A in FIG. 6, for an anterior insertion to provide correction for a cervical area vertebra in the sagittal plane, an implant device can be selected that has a wedge longitudinal angle in the range of about 2.5-7.5 degrees which will provide an overall alignment effect in the coronal plane of about 2.5-7.5 degrees. In some embodiments, the implant device and plate transverse angle is in the range of about 5-7.5 degrees and in some embodiments, the implant device and plate transverse angle is about 5 degrees.

It is understood, that if additional alignment correction is desired in the coronal plane, the intravertebral implant device may be selected with implant device transverse angles to provide this correction. This implant device transverse angle may be provided by either a plate transverse angle or a wedge transverse angle. For example, referring to Table A in FIG. 6 and utilizing the plate to provide the implant device transverse angle, for an anterior insertion to correct a lumbar area vertebra in the sagittal plane, an implant device can be selected that has a plate transverse angle in the range of about 1-20 degrees which will provide an overall alignment effect in the sagittal plane of about 1-20 degrees. In some embodiments, the device and plate transverse angle is in the range of about 5-15 degrees and in some embodiments, the device and plate transverse angle is about 10 degrees. Similarly, referring to Table A in FIG. 6, for a lateral insertion to provide additional correction for a thoracic area vertebra in the coronal plane, an implant device can be selected that has a plate transverse angle in the range of about 1-10 degrees which will provide an overall alignment effect in the coronal plane of about 1-10 degrees. In some embodiments, the implant device and plate transverse angle is in the range of about 5-10 degrees and in some embodiments, the implant device and plate transverse angle is about 5 degrees. Similarly, referring to Table A in FIG. 6, for a lateral insertion to provide additional correction for a cervical area vertebra in the coronal plane, an implant device can be selected that has a plate transverse angle in the range of about 1-5 degrees which will provide an overall alignment effect in the coronal plane of about 1-5 degrees. In some embodiments, the implant device and plate transverse angle is in the range of about 2.5-5 degrees and in some embodiments, the implant device and plate transverse angle is about 2.5 degrees.

Example Embodiments of Implant Devices to be Used with Oblique Insertion:

Example embodiment of intravertebral implant devices suitable for insertion from an oblique approach will be described below. Similar to the devices embodiments described above for lateral and anterior insertion, the difference in the devices used is generally in selecting different sized components to suit the direction of insertion, the spinal plane to be corrected and the area of the spine to be corrected. The uniqueness of insertion from an oblique direction is that the implant device must accommodate more complicated implant device surface plane angles.

The descriptions below utilize an implant device consistent with the embodiments described above and shown in FIGS. 2A and 2E. The descriptions below will utilize the dimensional examples shown in Table A of FIG. 6.

Oblique Insertion to Adjust Coronal Plane Alignment

One example embodiment of an intravertebral implant device suitable for insertion from an anterior approach to correct vertebral alignment in the coronal plane is described above and shown in FIGS. 1A and 1B.

For insertion from the oblique direction to correct spinal alignment in the coronal plane, an intravertebral implant device will be used that has a suitable implant device transverse and longitudinal angles to alter the vertebra surface planes as desired. These implant device surface plane angles may be provided by either transverse or longitudinal angles of the wedge or plate exterior surfaces or some combinations of these angles. For example, for a primarily coronal plane adjustment, the implant device surface plane angles are configured to primarily alter the vertebra surface planes in the coronal plane. With the oblique orientation of the implant device, to only alter the vertebra surface planes in the coronal plane, the plate transverse angle may vary along its length and the longitudinal angle may vary along its width. Similarly, the wedge may have a longitudinal angle that varies along its width and may have a wedge transverse angle that varies along its length. The resulting dimensions of the implant device, for a primarily coronal correction, should be configured to primarily alter the vertebra surface planes in the coronal plane.

For a simple illustration, without accounting for the variations of the plate and wedge angles along their width and length, an example of suitable dimensions is shown in Table A in FIG. 6. Utilizing the plate and the wedge to provide the implant device surface angles, for an oblique insertion to correct a lumbar area vertebra in the coronal plane, an implant device can be selected that has a plate transverse angle in the range of about 1-20 degrees and a wedge longitudinal angle in the range of about 5-20 degrees which will provide an overall alignment effect in the coronal plane of about 5-30 degrees. In some embodiments, the device and plate transverse angle is in the range of about 5-15 degrees and the implant device and wedge longitudinal angle is in the range of about 10-15 which will provide an overall alignment effect in the coronal plane of about 10-25 degrees. In some embodiments, the implant device and plate transverse angle is about 10 degrees and the wedge longitudinal angle is about 15 degrees which will provide an overall alignment effect in the coronal plane of about 20 degrees.

For use in the thoracic area, the intravertebral implant device will be similarly configured but will generally have smaller dimensions. For example, referring to Table A in FIG. 6, for an oblique insertion to provide correction for a thoracic area vertebra in the coronal plane, an implant device can be selected that has a plate transverse angle in the range of about 1-10 degrees and a wedge longitudinal angle in the range of about 5-15 degrees which will provide an overall alignment effect in the coronal plane of about 5-25 degrees. In some embodiments, the implant device and plate transverse angle is in the range of about 5-10 degrees and the longitudinal angle is in the range of about 10-15 degrees which will provide an overall alignment effect in the coronal plane of about 15-25 degrees. And in some embodiments, the implant device and plate transverse angle is about 5 degrees and the wedge longitudinal angle is about 10 degrees which will provide an overall alignment effect in the coronal plane of about 15 degrees.

Similarly, for use in the cervical area, the intravertebral implant device will be similarly configured but will generally have smaller dimensions. For example, referring to Table A in FIG. 6, for an oblique insertion to provide correction for a cervical area vertebra in the coronal plane, an implant device can be selected that has a plate transverse angle in the range of about 1-5 degrees and a wedge longitudinal angle in the range of about 2.5-7.5 degrees which will provide an overall alignment effect in the coronal plane of about 2.5-12.5 degrees. In some embodiments, the implant device and plate transverse angle is in the range of about 2.5-5 degrees and the longitudinal angle is in the range of about 5-7.5 degrees which will provide an overall alignment effect in the coronal plane of about 7.5-12.5 degrees. And in some embodiments, the implant device and plate transverse angle is about 2.5 degrees and the wedge longitudinal angle is about 5 degrees which will provide an overall alignment effect in the coronal plane of about 7.5 degrees.

For additional correction in the sagittal plane, the configuration of the implant device surface planes, as effected by the plate and wedge surface planes, can be selected to also alter the implant device and vertebra surface planes in the sagittal plane.

Oblique Insertion to Adjust Sagittal Plane Alignment

One example embodiment of an intravertebral implant device suitable for insertion from an anterior approach to correct vertebral alignment in the sagittal plane is described above and shown in FIGS. 2A and 2E.

As described above for insertion from the oblique direction to correct spinal alignment in the sagittal plane, for altering spinal alignment in the sagittal plane, an intravertebral implant device will be used that has a suitable device transverse and longitudinal angle to alter the vertebra surface planes as desired. These implant device surface plane angles may be provided by either transverse or longitudinal angles of the wedge or plate or combinations of these angles. For example, for a primarily sagittal plane adjustment, the implant device surface plane angles are configured to primarily alter the vertebra surface planes in the sagittal plane. With the oblique orientation of the implant device, to only alter the vertebra surface planes in the sagittal plane, the plate transverse angle may vary along its length and its longitudinal angle may vary along its width. Similarly, the wedge may have a longitudinal angle that varies along its width and may have a wedge transverse angle that varies along its length. The resulting dimensions of the implant device, for a primarily sagittal correction, should be configured to primarily alter the vertebra surface planes in the sagittal plane.

For a simple illustration, without accounting for the variations of the plate and wedge angles along their width and length, an example of suitable dimensions is shown in Table A in FIG. 6. Utilizing the plate and the wedge to provide the implant device surface angles, for an oblique insertion to correct a lumbar area vertebra in the sagittal plane, an implant device can be selected that has a plate transverse angle in the range of about 1-20 degrees and a wedge longitudinal angle in the range of about 5-20 degrees which will provide an overall alignment effect in the sagittal plane of about 5-30 degrees. In some embodiments, the implant device and plate transverse angle is in the range of about 5-15 degrees and the implant device and wedge longitudinal angle is in the range of about 10-15 which will provide an overall alignment effect in the sagittal plane of about 10-25 degrees. In some embodiments, the implant device and plate transverse angle is about 10 degrees and the wedge longitudinal angle is about 15 degrees which will provide an overall alignment effect in the sagittal plane of about 20 degrees.

For use in the thoracic area, the intravertebral implant device will be similarly configured but will generally have smaller dimensions. For example, referring to Table A in FIG. 6, for an oblique insertion to provide correction for a thoracic area vertebra in the sagittal plane, an implant device can be selected that has a plate transverse angle in the range of about 1-10 degrees and a wedge longitudinal angle in the range of about 5-15 degrees which will provide an overall alignment effect in the sagittal plane of about 5-25 degrees. In some embodiments, the implant device and plate transverse angle is in the range of about 5-10 degrees and the longitudinal angle is in the range of about 10-15 degrees which will provide an overall alignment effect in the sagittal plane of about 15-25 degrees. And in some embodiments, the implant device and plate transverse angle is about 5 degrees and the wedge longitudinal angle is about 10 degrees which will provide an overall alignment effect in the sagittal plane of about 15 degrees.

Similarly, for use in the cervical area, the intravertebral implant device will be similarly configured but will generally have smaller dimensions. For example, referring to Table A in FIG. 6, for an oblique insertion to provide correction for a cervical area vertebra in the sagittal plane, an implant device can be selected that has a plate transverse angle in the range of about 1-5 degrees and a wedge longitudinal angle in the range of about 2.5-7.5 degrees which will provide an overall alignment effect in the sagittal plane of about 2.5-12.5 degrees. In some embodiments, the implant device and plate transverse angle is in the range of about 2.5-5 degrees and the longitudinal angle is in the range of about 5-7.5 degrees which will provide an overall alignment effect in the sagittal plane of about 7.5-12.5 degrees. And in some embodiments, the implant device and plate transverse angle is about 2.5 degrees and the wedge longitudinal angle is about 5 degrees which will provide an overall alignment effect in the sagittal plane of about 7.5 degrees.

For additional correction in the coronal plane, the configuration of the device surface planes, as effected by the plate and wedge surface planes, can be selected to also alter the vertebra surface planes in the coronal plane.

Figure 7A:
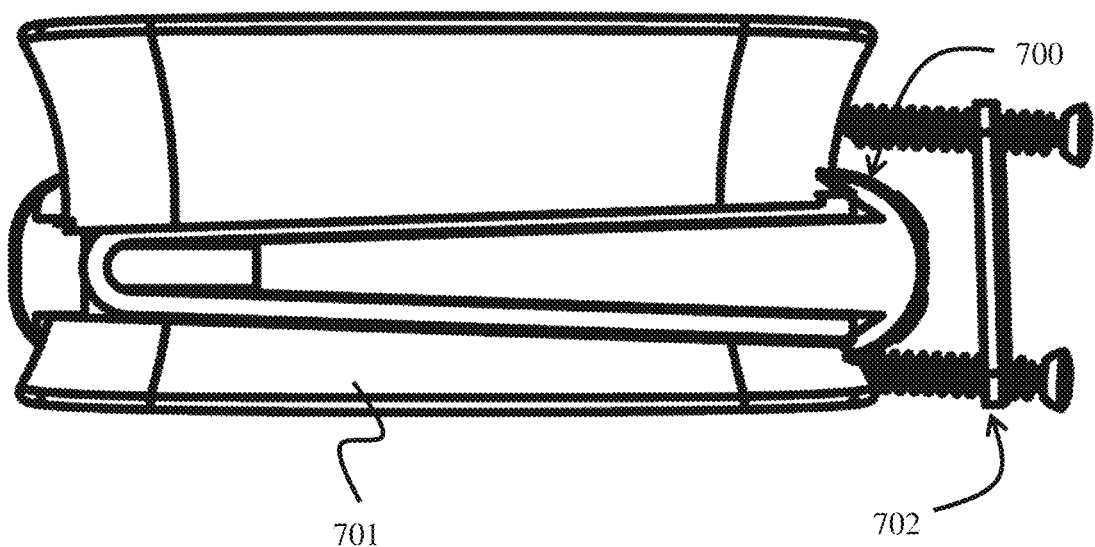
FIGS. 7A-7B illustrate example embodiments of components for use when inserting and securing the intravertebral implant device.
Figure 7B:
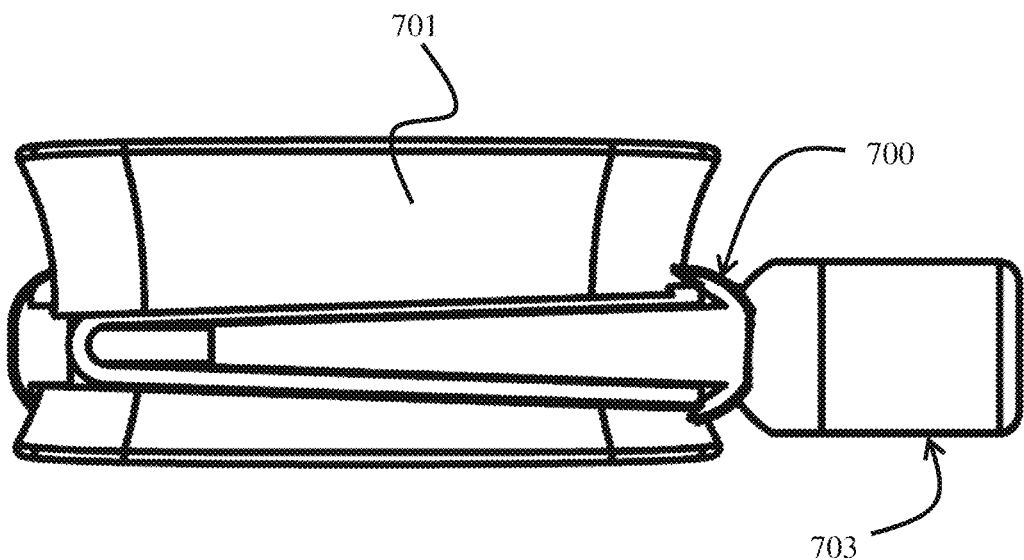

Additional Features of Embodiments of the Intravertebral Implant System:

FIGS. 7A and 7B show example embodiments of other components for the intravertebral implant system. FIG. 7A illustrates an example embodiment of a supplemental fixation device 702. As shown, the fixation device 702 comprises a securing plate and screws that may be secured to the bone to further secure the implant device 700 to the vertebra 701.

FIG. 7B illustrates an example embodiment of another supplemental device to couple to the implant system. For example, a connector 703 may be coupled to the implant device 700 by the nut or a screw to allow the implant system to be used as part of a larger construct. For example, as shown, the connector 703 may be coupled to the implant device 700 and configured to receive another device or component such that the intravertebral implant device 700 may be included in a longer construct such as a anterior rod or flexible cord (tether) anterior instrumentation system for correction of a longer multivertebra deformity.

In some embodiments, the wedge tines may be configured to provide supplemental fixation of the implant device to the vertebra. For example, the wedge tines may be extended and longer along the height of the wedge and through holes may extend through the wedge tine to allow a device such as a screw to further secure and affix the wedge and the implant device to the vertebra. In some embodiments, the intravertebral implant system further includes one or more navigation and robotic connections.

In some embodiments, the intravertebral implant system further includes one or more osteotomy guides.

In some embodiments, the intravertebral implant system further includes electro-field mechanisms. In these embodiments, a mechanism within the intravertebral implant may be activated by electromagnetic field, RFID, or other external field to cause the implant to produce a force on the fused vertebral body to change correction. This employs the effect of Wolff's Law where the bone responds to force to attain a level of stress, similar to orthodontia.

In some embodiments, the intravertebral implant system further includes percutaneous mechanisms. In these embodiments, a mechanism within the intravertebral implant may be activated by a percutaneous puncture of a tool to engage with the implant and cause the implant to create a force on the fused vertebral body to change correction. This also employs the effect of Wolff's Law where the bone responds to force to attain a level of stress, similar to orthodontia.

In some embodiments of the intravertebral implant system may be configured to provide non-surgical adjustment after the original surgery for further additional correction of the spine. These adjustments may be applied:
  In the immature developing spine, as growth can be accommodated, and correction adjusted.
  Where additional foraminal indirect decompression is needed.
  Where additional correction may be desired after the patient stands up.

In some embodiments, two implants can be placed side by side for increased strength and sagittal correction.

In some embodiments, a cortical bone graft can be placed alongside the implant(s) for a stronger fusion.

Although this invention has been described in the above forms with a certain degree of particularity, it is understood that the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention which is defined in the claims and their equivalents.

REFERENCES

Ahn, J., Tabaraee, E., Bohl, D. D., & Singh, K. (2017). Surgical management of adult spinal deformity: Indications, surgical outcomes, and health-related quality of life. Seminars in Spine Surgery, 29(2), 72-76. https://doi.org/10.1053/j.semss.2016.12.001.

Magerl, F., Aebi, M., Gertzbein, S. D., Harms, J., & Nazarian, S. (1994). A comprehensive classification of thoracic and lumbar injuries. European Spine Journal, 3(4), 184-201. https://doi.org/10.1007/BF02221591

We claim:

1. A vertebral implant device configured to alter an alignment of a spine, the vertebral implant device comprising:
a wedge;
a plate having a cavity configured to receive the wedge, a threaded through hole, an external surface configuration, and one or more plate tines;
a coupling device comprising a screw, wherein the screw further comprises a drive portion configured to be engaged by a drive tool and a distal threaded portion;
a staple having one or more staple tines;
the one or more plate tines and the one or more staple tines are configured to frictionally engage opposing sidewalls of a vertebral body;
the coupling device is configured to couple the wedge, the plate and the staple whereby when the vertebral implant device is secured in the vertebral body, the wedge affects the external surface configuration of the plate to alter a relative orientation of a superior endplate surface plane and an inferior endplate surface plane of the vertebral body and to alter the alignment of the spine;
wherein the threaded through hole of the plate engages the distal threaded portion of the screw whereby when the drive portion is rotated in a first rotation direction by the drive tool, the screw adjusts a device length of the vertebral implant device to secure the one or more plate tines and the one or more staple tines to the opposing sidewalls; and
wherein rotating the drive portion in the first rotation direction rotates the staple to position the one or more staple tines to engage one of the opposing sidewalls.

2. The vertebral implant device of claim 1 wherein:
the coupling device further comprises a nut;
the screw further comprises a screw swivel coupler; and
the staple comprises a staple swivel coupler to mate with the screw swivel coupler
whereby the staple is configured to swivel about a longitudinal axis of the screw.

3. The vertebral implant device of claim 2 wherein:
when the drive portion is rotated in the first rotation direction by the drive tool the screw adjusts the device length to a shorter length; and
the staple further comprises a proximal end having a radiused corner profile whereby when the drive portion is rotated in the first rotation direction by the drive tool, the proximal end of the staple engages the vertebral body to position the one or more staple tines to engage the one of the opposing sidewalls.

4. The vertebral implant device of claim 1 wherein the external surface configuration of the plate is defined by:
a plate longitudinal angle between a surface plane of a superior surface of the plate and a surface plane of an inferior surface of the plate; and
a plate height proximal to the one or more plate tines.

5. The vertebral implant device of claim 4 wherein the external surface configuration of the plate is further defined by a plate transverse angle between the surface plane of the superior surface of the plate and the surface plane of the inferior surface of the plate.

6. The vertebral implant device of claim 4 wherein:
the coupling device further comprises a nut;
the screw further comprises a screw swivel coupler;
the staple comprises a staple swivel coupler to mate with the screw swivel coupler whereby the staple is configured to swivel about a longitudinal axis of the screw;
the plate further comprises a two-pronged body defining the cavity configured to receive the wedge, the cavity further configured to receive the screw;
the screw is configured to be received in a bore of the wedge;
the nut is configured to be received in the bore of the wedge and couple to the screw whereby the screw and the nut secure the wedge in the cavity of the plate;
the external surface configuration of the plate is further defined by a plate transverse angle between the surface plane of the superior surface of the plate and the surface plane of the inferior surface of the plate;
the external surface configuration of the plate is further defined by an external surface configuration of the wedge whereby a device height of the vertebral implant device is affected by the external surface configuration of the wedge;
whereby when the drive portion is rotated in the first rotation direction by the drive tool, the screw adjusts the device length to a shorter length;
the staple further comprises a proximal end having a radiused corner profile whereby when the drive portion is rotated in the first rotation direction by the drive tool, the proximal end of the staple engages the vertebral body to position the one or more staple tines to engage the one of the opposing sidewalls;
the wedge comprises a plurality of wedges configured to be exchangeable with each other into engagement with the plate; and
each of the plurality of wedges having a different external surface configuration of the respective wedge.

7. The vertebral implant device of claim 1 wherein an external surface configuration of the wedge is defined by:
a wedge longitudinal angle between a surface plane of a superior surface of the wedge and a surface plane of an inferior surface of the wedge; and
a wedge height proximal to one or more wedge tines.

8. The vertebral implant device of claim 7 wherein the external surface configuration of the wedge is further defined by a wedge transverse angle between the surface plane of the superior surface of the wedge and the surface plane of the inferior surface of the wedge.

9. The vertebral implant device of claim 7 wherein:
the wedge comprises a plurality of wedges configured to be exchangeable with each other into engagement with the plate; and
each of the plurality of wedges having a different external surface configuration of the respective wedge.

10. The vertebral implant device of claim 1 wherein the coupling device is configured to adjust a device height of the vertebral implant device whereby an adjustment of the device height alters the external surface configuration of the plate and alters the relative orientation of the superior endplate surface plane and the inferior endplate surface plane of the vertebral body.

11. The vertebral implant device of claim 1 wherein:
the coupling device further comprises a nut;
the plate further comprises a two-pronged u-shaped body defining the cavity configured to receive the wedge, the cavity further configured to receive the screw;
the screw is configured to be received in a bore of the wedge; and the nut is configured to be received in the bore of the wedge and couple to the screw whereby the screw and the nut secure the wedge in the cavity of the plate.

12. The vertebral implant device of claim 11 wherein:
the two-pronged u-shaped body comprises an angularly flexible body;
the angularly flexible body is affected by an external surface configuration of the wedge; and
a device height of the vertebral implant device is affected by the external surface configuration of the wedge.

13. The vertebral implant device of claim 1 wherein the coupling device further comprises a nut.

14. The vertebral implant device of claim 1 wherein:
the screw further comprises a screw swivel coupler;
the staple comprises a staple swivel coupler to mate with the screw swivel coupler whereby the staple is configured to swivel about a longitudinal axis of the screw; and
the staple further comprises a proximal end having a radiused corner profile whereby when the drive portion is rotated in the first rotation direction, the proximal end of the staple engages the vertebral body to stop a further rotation of the staple.

15. A vertebral implant system configured to alter an alignment of a spine, the vertebral implant system comprising:
a vertebral implant device comprising:
a staple having one or more staple tines;
a wedge;
a plate having a cavity configured to receive the wedge, a threaded through hole, an external surface configuration, and one or more plate tines;
a coupling device comprising a screw, wherein the screw further comprises a drive portion configured to be engaged by a drive tool and a distal threaded portion;
the one or more plate tines and the one or more staple tines are configured to frictionally engage opposing sidewalls of a vertebral body;
the coupling device is configured to couple the wedge, the plate and the staple whereby when the vertebral implant device is secured in the vertebral body, the wedge affects the external surface configuration of the plate to alter a relative orientation of a superior endplate surface plane and an inferior endplate surface plane of the vertebral body and to alter the alignment of the spine;
wherein the threaded through hole of the plate engages the distal threaded portion of the screw whereby when the drive portion is rotated in a first rotation direction by the drive tool, the screw adjusts a device length of the vertebral implant device to secure the one or more plate tines and the one or more staple tines to the opposing sidewalls; and
wherein rotating the drive portion in the first rotation direction rotates the staple to position the one or more staple tines to engage one of the opposing sidewalls;
the system further comprising a set of wedges from which the wedge is selected;
the set of wedges comprising at least a first wedge and a second wedge wherein the first wedge has a first external dimension and the second wedge has a second external dimension; and
the plate configured to receive either the first wedge or the second wedge whereby:
when the first wedge is received in the plate, a first implant device external dimension is created to alter the relative orientation of the superior endplate surface plane and the inferior endplate surface plane of the vertebral body and to alter the alignment of the spine to a first degree, and
when the second wedge is received in the plate, a second implant device external dimension is created to alter the relative orientation of the superior endplate surface plane and the inferior endplate surface plane of the vertebral body and to alter the alignment of the spine to a second degree.

16. The vertebral implant system of claim 15 wherein the plate comprises at least a first plate and a second plate wherein:
the first plate has a first external surface configuration;
the second plate has a second external surface configuration; and
the first plate and the second plate are exchangeable whereby:
when the first wedge is received in the first plate, a third implant device external dimension is created to alter the relative orientation of the superior endplate surface plane and the inferior endplate surface plane of the vertebral body and to alter the alignment of the spine to a third degree, and
when the first wedge is received in the second plate, a fourth implant device external dimension is created to alter the relative orientation of the superior endplate surface plane and the inferior endplate surface plane of the vertebral body and to alter the alignment of the spine to a fourth degree.

17. The vertebral implant system of claim 15 wherein:
the plate comprises at least a first plate and a second plate;
the first wedge is received in the first plate whereby the first implant device external dimension is defined by:
a first plate longitudinal angle between a surface plane of a superior surface of the first plate and a surface plane of an inferior surface of the first plate, and
a first plate height of the first plate; and
the second wedge is received in the second plate whereby the second implant device external dimension is defined by:
a second plate longitudinal angle between a surface plane of a superior surface of the second plate and a surface plane of an inferior surface of the second plate, and
a second plate height of the second plate.

18. The vertebral implant system of claim 15 wherein:
the first implant device external dimension is defined by:
a first wedge longitudinal angle between a surface plane of a superior surface of the first wedge and a surface plane of an inferior surface of the first wedge,
a plate thickness, and
a plate height; and
the second implant device external dimension is defined by:
a second wedge longitudinal angle between a surface plane of a superior surface of the second wedge and a surface plane of an inferior surface of the second wedge,
the plate thickness, and
the plate height.

19. A method to alter an alignment of a spine, the method comprising:
performing an osteotomy procedure through a vertebral body inferior to a pedicle of the vertebral body;
providing a vertebral implant device comprising:
a wedge, a plate having a cavity configured to receive the wedge, a threaded through hole, an external surface configuration, and one or more plate tines, a coupling device comprising a screw, wherein the screw further comprises a drive portion configured to be engaged by a drive tool and a distal threaded portion, a staple having one or more staple tines, and the coupling device is configured to couple the wedge, the plate and the staple whereby when the vertebral implant device is secured in the vertebral body, the wedge affects the external surface configuration of the plate to alter a relative orientation of a superior endplate surface plane and an inferior endplate surface plane of the vertebral body and to alter the alignment of the spine;

inserting the plate and the staple into a vertebral opening created by the osteotomy procedure;

deploying the staple whereby the staple extends outside of the vertebral opening;

rotating the drive portion of the screw in a first rotation direction by the drive tool to rotate the staple whereby the one or more staple tines are positioned generally perpendicular to the osteotomy to engage a sidewall of the vertebral body;

engaging the threaded through hole of the plate with the distal threaded portion of the screw;

tightening the screw coupled to the staple by rotating the drive portion in the first rotation direction by the drive tool to adjust a device length of the vertebral implant device whereby the one or more staple tines are drawn towards the plate such that the one or more plate tines and the one or more staples tines frictionally engage opposing sidewalls of the vertebral body;

positioning the wedge over a proximal end of the screw and into the cavity of the plate;

coupling a nut on the proximal end of the screw and into a bore of the wedge;

tightening the nut on the screw whereby the plate is distracted by the wedge as it is drawn into the vertebral body; and further tightening the nut onto the screw whereby the wedge is secured within the cavity of the plate defining the external surface configuration of the plate to alter the relative orientation of the superior endplate surface plane and the inferior endplate surface plane of the vertebral body and to alter the alignment of the spine.

* * * * *